US007145055B2

(12) United States Patent
Ito et al.

(10) Patent No.: US 7,145,055 B2
(45) Date of Patent: Dec. 5, 2006

(54) METHOD OF PRODUCING A MOUSE SUITABLE FOR THE ENGRAFTMENT, DIFFERENTIATION AND PROLIFERATION OF HETEROLOGOUS CELLS, MOUSE PRODUCED BY THIS METHOD AND USE OF THE MOUSE

(75) Inventors: Mamoru Ito, Kanagawa (JP); Kimio Kobayashi, Kanagawa (JP); Tatsutoshi Nakahata, Kyoto (JP); Koichiro Tsuji, Tokyo (JP); Sonoko Habu, Tokyo (JP); Yoshio Koyanagi, Chiba (JP); Naoki Yamamoto, Tokyo (JP); Kazuo Sugamura, Miyagi (JP); Kiyoshi Ando, Kanagawa (JP); Tatsuji Nomura, Tokyo (JP)

(73) Assignee: Central Institute for Experimental Animals, Kanagawa (JP)

( * ) Notice: Subject to any disclaimer, the term of this patent is extended or adjusted under 35 U.S.C. 154(b) by 198 days.

(21) Appl. No.: 10/221,549

(22) PCT Filed: Oct. 25, 2001

(86) PCT No.: PCT/JP01/09401

§ 371 (c)(1),
(2), (4) Date: Sep. 10, 2002

(87) PCT Pub. No.: WO02/43477

PCT Pub. Date: Jun. 6, 2002

(65) Prior Publication Data

US 2003/0182671 A1 Sep. 25, 2003

(30) Foreign Application Priority Data

Dec. 1, 2000 (JP) .............................. 2000-367296

(51) Int. Cl.
 G01N 33/00 (2006.01)
 C12N 15/01 (2006.01)
 A01K 67/02 (2006.01)
 A01K 67/027 (2006.01)

(52) U.S. Cl. .............................. 800/3; 800/18; 800/21; 800/22

(58) Field of Classification Search .................... 800/3, 800/18, 22
See application file for complete search history.

(56) References Cited

FOREIGN PATENT DOCUMENTS

JP  9-94040 A   4/1997
JP  3753321     12/2005

WO  WO 99/60846  12/1999

OTHER PUBLICATIONS

Dermer G.B. Another Anniversary for the war on cancer. (1994) Bio/Technol. 12:320.*
Demirci et al. Islet allograft rejection in nonobese diabetic mice involves the common gamma-chain and CD28/CD154-dependent and -independent mechanisms. J Immunol. Oct. 1, 2003;171(7):3878-85.*
Doetschman T. Interpretation of phenotype in genetically engineered mice. Lab Anim Sci. Apr. 1999;49(2):137-43.*
Gallegos et al. Driven to autoimmunity: the nod mouse. Cell. Apr. 16, 2004;117(2):149-51.*
Gromeier et al. Viruses for the treatment of malignant glioma. Curr Opin Mol Ther. Oct. 2001;3(5):503-8.*
Gura T. Systems for identifying new drugs are often faulty. Science. Nov. 7, 1997;278(5340):1041-2.*
Holschneider et al. Genotype to phenotype: challenges and opportunities. Int J Dev Neurosci. Oct. 2000;18(6):615-8.*
Lewis et al. Developing animal models for AIDS research—progress and problems. Trends Biotechnol. Apr. 1995;13(4):142-50.*
Imada et al. Serial transplantation of adult T cell leukemia cells into severe combined immunodeficient mice. Jpn J Cancer Res. Sep. 1996;87(9):887-92.*
Fukao et al. Expression of functional IL-2 receptors on mature splenic dendritic cells. Eur J Immunol. May 2000;30(5):1453-7.*
Brathia, M. et al., "A newly discovered class of human hematopoietic cells with SCID-repopulating activity" *Nature Medicine* 4(9):1038-1045 (Sep. 1998).
Christianson, S. et al., "Enhanced Human $CD4^+$Cell Engraftment in β2-Microglobulin-Deficient NOD-scid Mice" *The Journal of Immunology* 3578-3586 (1997).
Goldman , J. et al. "Enhanced human cell engraftment to mice deficient in RAG2 and the common cytokine receptor γ chain", *Bristish Journal of Immunology* 103:335-342.
Greiner, . et al. SCID Mouse Models of Human Stem Cell Engraftment *Stem Cells* 16:166-177 (1998).
Kollet, O. et al., "β2 Microglobulin-deficient (B2m$^{null}$) NOD/SCID mice excellent recipients for studying human stem cell function"*Blood*, 95(10):3102-3105 (2000).
Koyanagi, et al., "Primary Viremia and CNS Invasion with HIV-1 in a Novel hu-PBL Immunideficient Mouse Strain" *Folia Microbiologia* 71(3):2417-2424 (1997) (abstract).

(Continued)

*Primary Examiner*—Daniel M. Sullivan
(74) *Attorney, Agent, or Firm*—Ginger R. Dreger; Heller Ehrman LLP

(57) ABSTRACT

The present invention provides an immunodeficient mouse (NOG mouse) suitable for engraftment, differentiation and proliferation of heterologous cells, and a method of producing such a mouse. This mouse is obtained by backcrossing a C.B-17-scid mouse with an NOD/Shi mouse, and further backcrossing an interleukin 2-receptor γ-chain gene-knockout mouse with the thus backcrossed mouse. It is usable for producing a human antibody and establishing a stem cell assay system, a tumor model and a virus-infection model.

14 Claims, 28 Drawing Sheets

OTHER PUBLICATIONS

Koyanagi, Y. et al.,"Primary Human Immunideficiency Virus Type 1 Viremia and Central Nervous System Invasion in a Novel hu-PBL-Immunideficient Mouse Strain" *Journal of Virology* 71(3):2417-2423 (1997).

Ohbo, K. et al., "Modullation of Hematopoesis in MICE With a Truncated Mutant of the Interleukin-2 Receptor γ Chain" *Blood* 87(3):956-967 (1996).

Reifsnyder, P.C. et al., "Genotypic and phenotypic characterization of six new recombinant congenic strains derived from NOD/*Shi* and CBA/J genomes" *Mammalian Genome* 10:161-167 (1999).

Schultz, L. et al., "NOD/LtSZ-Rad 1 $^{null}$ Mice: An Immunod-deficient and Radioresistant Model for Engrafment of Human Hematolymphoid Cells, HIV Infection, and Adoptive Transfer of NOD Mouse Diabetogenic T Cells". *Journal of Immunology* 2496-2507 (2000).

Serreze, D., et al. "Emv30$^{null}$ NOD-scid Mice" *Diabetes* 44:1302-1398 (Dec. 1995).

Ito, et al., "NOD/SCID/γc$^{null}$ mouse: an excellent recipient mouse model for engraftment of human cells ", BLOOD, vol. 100(6); pp. 3175-3182; (Nov. 2002).

Suzuki, Haruhiko, et al., "Deregulated T Cell Activation and Autoimmunity in Mice Lacking Interleukin-2 Receptor β", Science vol. 268, pp. 14721476 (Jun. 1995).

Takashi, Saitoh, et al., additional volume of Experimental Medicine, Bio Science Library of Terms, Immunology, pp. 198-200 (1998)—English translation of Exhibit D.

Chan, Camie W., et al., "Interferon-producing Killer Dendritic Cells Provide a Link Between Innate and Adaptive Immunity", Nature Medicine, vol. 12, No. 2, pp. 207-213 (Feb. 2006).

Taieb, Julien, et al., "A Novel Dendritic Cell Subset Involved in Tumor Immunosurveillance", Nature Medicine, vol. 12, No. 2, pp. 214-219 (Feb. 2006).

Nakata, Hirotomo, et al., "Potent Anti-R5 Human Immunodeficiency Virus Type 1 Effects of a CCR5 Antagonist, AK602/ONO4128/GW873140, in a Novel Human Peripheral Blood Mononuclear Cell Nonobese Diabetic-SCID, Interleukin-2 Receptor γ-Chain Knocked-Out AIDS Mouse Model", Journal of Virology, vol. 79, No. 4, pp. 2087-2096 (Feb. 2005).

* cited by examiner

FIG. 2A

| Posttrans-plantation | mouse | | hCD45+(%) | hCD45+(/μl) | hCD41+(%) | hCD41+(/μl) |
|---|---|---|---|---|---|---|
| 4th week | I 8 mice | Mean | 1.345 | 12.503 | 0.037 | 387.087 |
| | | SE | 0.281 | 2.683 | 0.013 | 144.057 |
| | II 8 mice | Mean | 8.585 | 79.116 | 0.384 | 3096.365 |
| | | SE | 1.668 | 21.701 | 0.138 | 647.664 |
| 8th week | I 8 mice | Mean | 6.623 | 81.513 | 0.086 | 590.814 |
| | | SE | 3.097 | 33.896 | 0.053 | 349.314 |
| | II 8 mice | Mean | 37.152 | 533.456 | 0.380 | 2422.976 |
| | | SE | 7.324 | 99.283 | 0.112 | 547.911 |
| 12th week | I 7 mice | Mean | 5.860 | 61.999 | 2.064 | 1510.084 |
| | | SE | 2.395 | 22.302 | 1.308 | 769.132 |
| | II 6 mice | Mean | 24.086 | 530.097 | 2.586 | 2227.427 |
| | | SE | 5.789 | 281.806 | 0.600 | 466.970 |

Mouse I: NOD/Shi-scid + antiAGM1
Mouse II: NOG primary recipient secondary recipient tertiary recipient

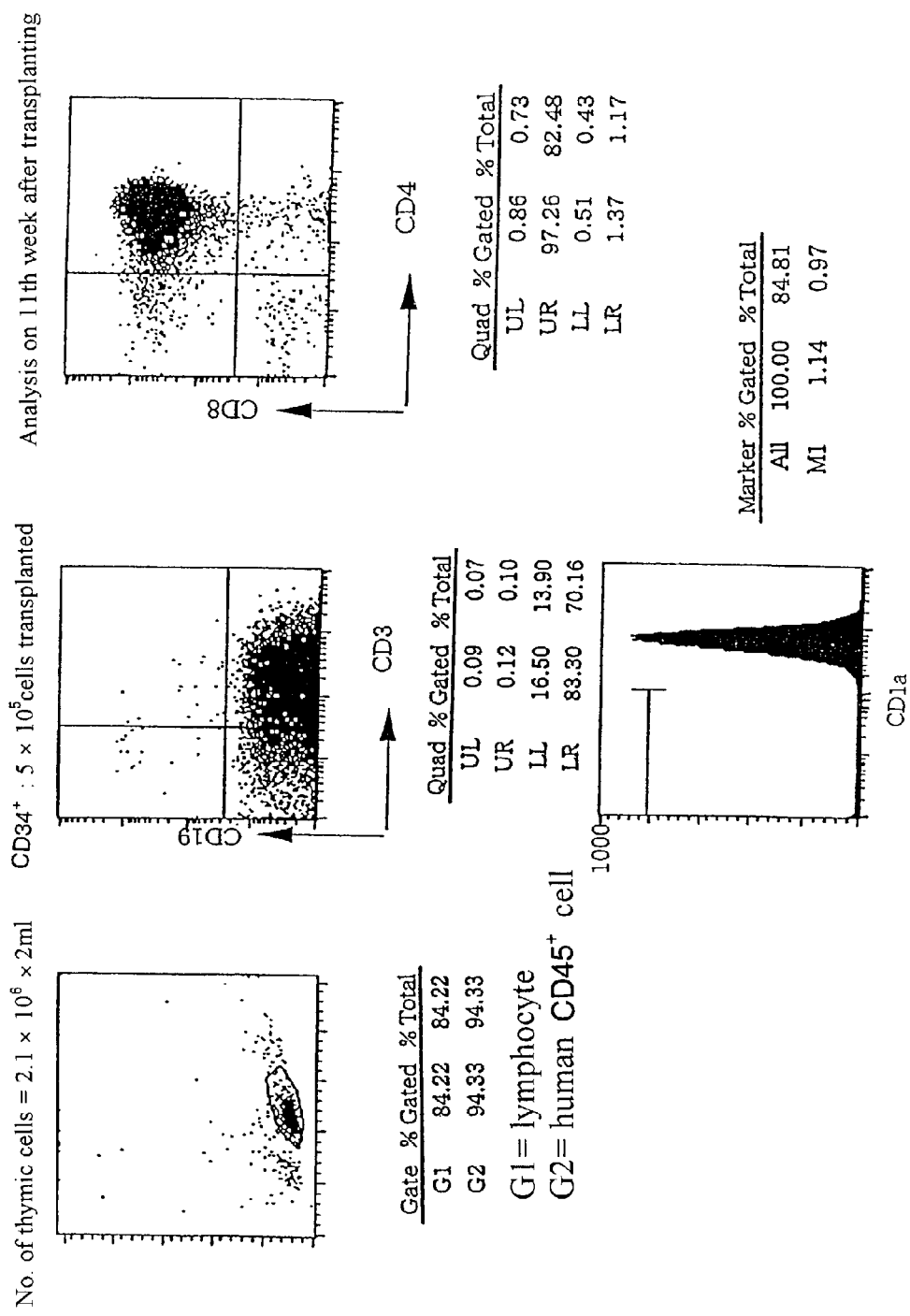
FIG.9A Flowcytometric Analysis of thymic cells

Flowcytometric Analysis of peripheral blood

G1= lymphocyte
G2= human CD45⁺ cell

11th week after transplanting CD34

| Quad | % Gated | % Total |
|------|---------|---------|
| UL | 21.46 | 0.22 |
| UR | 0.10 | 0.00 |
| LL | 77.97 | 0.81 |
| LR | 0.48 | 0.01 |

| Quad | % Gated | % Total |
|------|---------|---------|
| UL | 36.19 | 1.75 |
| UR | 0.06 | 0.00 |
| LL | 60.66 | 2.93 |
| LR | 3.09 | 0.15 |

Flowcytometric Analysis of peripheral blood

G1 = lymphocyte
G2 = human CD45$^+$ cell

13th week after transplanting CD34

| Quad | % Gated | % Total |
|------|---------|---------|
| UL | 3.77 | 0.67 |
| UR | 0.18 | 0.03 |
| LL | 90.34 | 16.12 |
| LR | 5.72 | 1.02 |

| Quad | % Gated | % Total |
|------|---------|---------|
| UL | 31.41 | 3.40 |
| UR | 0.02 | 0.00 |
| LL | 55.11 | 5.97 |
| LR | 13.46 | 1.46 |

Flowcytometric Analysis of bone marrow cells

METHOD OF PRODUCING A MOUSE SUITABLE FOR THE ENGRAFTMENT, DIFFERENTIATION AND PROLIFERATION OF HETEROLOGOUS CELLS, MOUSE PRODUCED BY THIS METHOD AND USE OF THE MOUSE

TECHNICAL FIELD

The present invention relates to a method of producing an excellent mouse for engraftment of heterologous cells, a mouse produced by this method and use of the mouse.

BACKGROUND ART

Laboratory animals to which heterologous cells including human cells are engrafted are very important for analysis of onset mechanisms of various diseases and drug developments for the treatments or preventions thereof, and development of animals as receptors therefor is one of major themes in laboratory animal sciences. In particular, in recent years, treatments etc. (known as regenerative medicine) in which tissues or cells differentiated from stem cells are transplanted have received world-wide attention, and therefore these animals are of increasing importance.

The inventors of the present invention have continued to develop and improve these laboratory animals. In particular, they made improvements or the like on a nude mouse or a SCID mouse, and they have already filed a patent application (Japanese Patent Application Laying-Open (kokai) No. 9-94040) concerning an immunodeficient mouse etc. produced for this purpose. Above all, an NOD/Shi-scid mouse and an NOD/LtSz-scid mouse which exhibit multifunctional immunodeficiency (functional deficiency of T cells and B cells, decline of macrophage function, reduction of complement activity, reduction of natural killer (NK) activity etc.) are the most noteworthy as laboratory animals suitable for engraftment of heterologous cells. Since it became clear that they could be used for various types of research including stem cell differentiation and proliferation, the range of applications in which they are used has increased to the present level.

However, human cells are engrafted to the NOD/Shi-scid mouse at a high ratio, but it is recognized that the engraftment capacity is substantially varied.

In order to enhance the engraftment capacity of the NOD/Shi-scid mouse, it has already been revealed that reduction of NK activity in the mouse by administering anti IL-2Rβ chain antibodies (TMβ1), anti-asialo-GM1 antibodies or the like is important. (Koyanagi, Y. et al., 1997. "Primary human immunodeficiency virus type 1 viremia and central nervous system invasion in a novel hu-PBL-immunodeficient mouse strain." J Virol 71:2417; Koyanagi, Y. et al., 1997. "High levels of viremia in hu-PBL-NOD-scid mice with HIV-1 infection." Leukemia 11 Suppl. 3:109; Yoshino H, et al., 2000. "Natural killer cell depletion by anti-asialo GM1 antiserum treatment enhances human hematopoietic stem cell engraftment in NOD/Shi-scid mice." Bone Marrow Transplant 26:1211–6. However, these antibodies are very expensive, and it is recognized that their efficacies vary between individuals. Further, when anti-asialo GM1 antibodies are used, the administration thereof should be conducted with the frequency of every eleventh day during the experiment period, and thus a degree of complexity is attached.

Therefore, Dr. Shultz, L. D. et al. of The Jackson Laboratory in the United States produced an NOD/LtSz-scid, β2m null(β2m (null) NOD/SCID)mouse (Kollet O, Peled A, Byk T et al., beta2 microglobulin-deficient (β2m(null)) NOD/SCID mice are excellent recipients for studying human stem cell function. Blood 2000;95(10):3102–5) by crossing an NOD/LtSz-scid mouse having high engraftment capacity of human cells with a β2m KO mouse from which NK activity has been depleted.

With respect to the NOD/LtSz-scid, β2m null mouse, T cells, B cells and natural killer (NK) cells are depleted, and the function of macrophages and complements is reduced. However, other cells (e.g. dendritic cells) and factors (e.g. IFNγ) are also involved in the rejection of transplanted heterologous cells or tissues.

Accordingly, a mouse which, compared to the NOD/LtSz-scid, β2m null mouse, has no variation in heterologous cell engraftment capacity, requires no antibodies, and has excellent heterologous cell engraftment is desirable.

DISCLOSURE OF THE INVENTION

Thus, the object of the present invention is to solve the above problems and to provide a method of producing a mouse having excellent heterologous cell engraftment capacity and a mouse produced by the same method.

The present inventors have made intensive studies to solve the above problems. As a result, they have obtained the findings that a mouse which has no variation in engraftment capacity of heterologous cells and requires no antibodies (that is, is suitable for the engraftment of heterologous cells) can be obtained by backcrossing an NOD/Shi mouse with a C.B-17-scid mouse, and further backcrossing the thus obtained mouse with an interleukin 2-receptor γ-chain (IL-2Rγ) gene-knockout mouse. The present invention has been accomplished based on the above findings.

Namely, the present invention is as follows.

(1) A method of producing a mouse suitable for engraftment of heterologous cells, comprising backcrossing a mouse B with a mouse A, as described below:

A: a mouse obtained by backcrossing a C.B-17-scid mouse with an NOD/Shi mouse; and B: an interleukin 2-receptor γ-chain (IL-2Rγ) gene knockout mouse.

(2) The method of producing a mouse as described in (1), wherein the mouse A is an NOD/Shi-scid mouse.

(3) The method of producing a mouse as described in (1) or (2), wherein the mouse B is an IL-2RγKO mouse.

(4) A mouse produced by the method of producing a mouse described in any of (1) to (3).

(5) A NOG (NOD/Shi-scid, IL-2Rγ KO) mouse having excellent engraftment capacity of heterologous cells, wherein both of functional T-cells and functional B-cells are deleted, macrophage function is reduced, NK cells or NK activity are eliminated, dendritic cell function is reduced.

(6) The NOG mouse described in (4) or (5), wherein transplanted human stem cells efficiently differentiate and proliferate without being eliminated.

(7) A stem cell assay method comprising transplanting human stem cells to the mouse described in any of (4) to (6) and analyzing the differentiated and proliferated cells.

(8) The stem cell assay method described in (7), comprising analyzing the differentiation and proliferation of T-cells and B-cells.

(9) A method of proliferating human stem cells comprising:

transplanting and proliferating the human stem cells to the mouse described in any of (4) to (6);

collecting the human stem cells from bone marrow of the mouse; and repeatedly transplanting the collected cells to the mouse described in any of (4) to (6).

(10) The method of proliferating human stem cells described in (9), wherein the frequency of repeating is at least three times.

(11) Human stem cells obtained by the method of (9) or (10), wherein the obtained human stem cells have a purity of 99.7% or more.

(12) The method described in (9) or (10), wherein the human stem cells have foreign genes introduced thereinto.

(13) The mouse described in any of (4) to (6), wherein the mouse is capable of stably retaining human T-cells and B cells and producing a human antibody.

(14) A method of producing a human antibody comprising immunizing with an antigen the mouse described in any of (4) to (6) which retains human T-cells and B-cells.

(15) A method of producing an antibody-producing cell line which produces a human antibody, comprising:

immunizing with an antigen the mouse described in any of (4) to (6) which retains human T-cells and B-cells;

collecting from the mouse cells which produce the antibody against the antigen; and establishing a cell line.

(16) A human tumor model mouse wherein the mouse is a mouse described in any of (4) to (6) and retains human tumor cells.

(17) The human tumor model mouse described in (16), wherein the human tumor cells are derived from HTLV-1 leukemia.

(18) The human tumor model mouse described in (16) or (17), wherein the mouse has the human tumor cells at an auricle thereof.

(19) A method of screening an anticancer agent using the mouse described in any of (16) to (18).

(20) A method of producing a human tumor model mouse comprising transplanting human tumor cells to the mouse described in any of (4) to (6).

(21) The method described in (16), wherein the human tumor cells are derived from HTLV-1 leukemia.

(22) The method described in (20) or (21), wherein the human tumor cells are transplanted at an auricle of the mouse.

(23) A virus-infected model mouse wherein the mouse is a mouse described in any of (4) to (6) and retains T cells infected with a T-tropic (T-cell affinity) virus as well as a macrophage-tropic virus.

(24) The virus-infected model mouse described in (23), wherein the virus is HIV.

(25) The virus-infected model mouse described in (23), wherein the virus is HTLV-1.

(26) A method of screening an antiviral agent wherein the method is carried out using the mouse described in (23) to (25).

(27) A method of producing an immunodeficient mouse which has engraftment capacity of enhanced heterologous cells compared with a NOG mouse, wherein the method is carried out using the mouse described in (3) to (6).

(28) The mouse described in (3) to (6), wherein the mouse is used for producing an immunodeficient mouse which has enhanced engraftment capacity of heterologous cells compared with a NOG mouse.

Hereinafter, general embodiments of the present invention will be described.

1. Production of a Mouse of the Present Invention

According to the present invention, a method of producing a mouse suitable for the engraftment of heterologous cells is characterized in backcrossing a mouse B with a mouse A, as described below.

A: a mouse obtained by backcrossing a C.B-17-scid mouse with an NOD/Shi mouse; and B: an interleukin 2-receptor γ-chain gene knockout mouse.

Here, examples of the heterologous cells include cells or tissues derived from mammals such as humans, mice, rats etc., particularly human stem cells, lymphocytes or tumor cells etc. of humans, but not limited thereto.

With respect to the mouse A, backcrossing the C.B-17-scid mouse with the NOD/Shi mouse is done in accordance with methods well-known to a person skilled in the art, for example, backcrossing by Cross Intercross method (Inbred Strains in Biomedical Research, M. F. W. Festing, 1979, ISBN 0-333-23809-5, The Macmillan Press, London and Basingstoke). The C.B-17-scid mouse is crossed with the NOD/Shi mouse, and the obtained F1 mice are further crossed with each other. Then, the immunoglobulin amount in blood serum of the thus obtained F2 mice is measured for selecting a mouse, from which immunoglobulin cannot be detected. The selected mouse is again crossed with a NOD/Shi mouse. Repeating this process (Cross Intercross method) 9 times or more enables the accomplishment of the backcrossing.

A NOD/Shi mouse and a C.B-17-scid mouse are both commercially available from CLEA JAPAN, INC. Further, examples of mice obtained by crossing these mice with each other include a NOD/Shi-scid mouse (also called as a NOD-scid mouse) (Japanese Patent Application Laying-Open (kokai) No. 9-94040) which the present inventors have already established. This mouse is purchased from CLEA JAPAN, INC., and can be used directly as the mouse A. In addition, the present inventors possess, other than the ones mentioned above, NOD/Shi mice and NOD/Shi-scid mice, which can be split up and provided whenever the need arises.

Moreover, with respect to the mouse B, knockout of an interleukin 2-receptor γ-chain (IL-2Rγ) gene is carried out in accordance with methods well known to a person skilled in the art, for example, a homologous recombination method using mouse ES cells (Capecchi, M. R., Altering the genome by homologous recombination, Science, (1989) 244, 1288–1292). After substituting a specific mouse-derived gene by a homologous gene including a gene resistant to a drug, for example neomycin etc. at ES cell stage, the ES cells are inserted into a fertilized egg, thereby accomplishing the gene-knockout.

Specifically, for example, gene clones containing a mouse IL-2Rγ are isolated, from a genome library of 129/SV mouse, using a human IL-2RγcDNA as a probe. Using a fragment of 8.6 kb containing the full length of IL-2Rγ among the clones, a targeting vector is prepared. That is, PMCl-neo poly A which expresses a neomycin resistant gene, is inserted between exons 7 and 8 of IL-2R in the fragment, and also a diphtheria toxin-A gene is placed at 3' side 1 kb away from exon 8. Next, the vector is made linear, and introduced into $1 \times 10^7$ of E14 ES cells by electroporation. Thereafter, ES clones which bring about homologous recombination in the culture solution including G418, are selected (confirmed by PCR or Southern method), and after injecting the ES clones into blastocysts of C57BL/6 mice, they are transplanted into the uteruses of foster parent mice. Chimeric mice born from the foster parent mice are further crossed with C57BL/6 mice, thereby obtaining IL-2RγKO hetero mice wherein knockout is transduced to germ cells.

Alternatively, pre-established interleukin-2 receptor γ chain gene (IL-2Rγ) knockout mouse strain may directly be obtained for use from suppliers, and examples of the mouse strains include interleukin-2 receptor γ chain (IL-2Rγ) knockout mice (Ohbo K, Suda T, Hashiyama M et al., Modulation of hematopoiesis in mice with a truncated mutant of the interleukin-2 receptor gamma chain. Blood 1996;87(3):956–67)) which was produced from IL-2RγKO mouse strains [Prof. Kazuo Sugamura, Department of Microbiology and Immunology, Tohoku University School of Medicine]. Incidentally, IL-2RγKO mice are presently stored in the embryo preservation bank of the applicants (Central Institute for Experimental Animals) at the request of Prof. Sugamura, a producer of the mouse strain, and whenever the need arises they can be provided as frozen embryos or as thaw-reconstruction mice.

Further, backcrossing the mouse B with the mouse A can be carried out, in similar fashion as described above, according to conventional methods well-known to a person skilled in the art. For example, in accordance with the above backcrossing, that is, a NOD/Shi-scid mouse is crossed with an IL-2RγKO mouse, and the obtained F1 mouse is back-crossed with an NOD/Shi-scid mouse, thereby accomplishing the backcross.

Furthermore, a mouse of the present invention is characterized in that the mouse is produced by the above method of the present invention. The mouse of the present invention is referred to as a NOG mouse (NOG mouse; NOD/Shi-scid, γc null mouse; NOD/Shi-scid, IL-2Rγ chain–/–mouse; NOD/Shi-scid, IL-2R(γc)$^{null}$ mouse etc.)

The mouse of the present invention is a severe immunodeficient mouse in which has both of functional T-cells and functional B-cells are deleted, macrophage function are reduced, and NK cells or NK activity are eliminated. Therefore, when heterologous cells (e.g. human peripheral blood mononuclear leukocytes) are introduced into the mouse of the present invention, much higher ratios of engraftment and proliferation are observed even in comparison with conventional immunodeficient mice which are subjected to anti NK antibody treatment. (See Example 1 described below) Further, dendritic cells of the mouse of the present invention are also functionally incompetent, and the production of cytokine is remarkably reduced. Thus, the mouse of the present invention has the most excellent engraftment capacity of heterologous cells as compared with conventional immunodeficient mice, and it is considered effective for analyses of various introduced heterologous cells (including stem cells, differentiated cells and cancer cells) which are engrafted in this mouse. Additionally, it is possible to use the mouse in order to establish a pathologic model mouse and produce a human antibody for HIV, HTLV-1 or cancer.

Hereinafter, the applications of the mouse of the present invention will be described. Usually, the mouse to be used is preferably 8 to 12 weeks old, but not limited thereto.

2. Establishment of Human Stem Cell Assay System Using the Mouse of the Present Invention Using the mouse of the present invention, it is possible to establish a human stem cell assay system for examining factors and mechanisms which are engaged in differentiation and proliferation of human stem cells. Also, it is possible to research various therapeutic products using the human stem cell assay system.

Introducing human stem cells into the mouse of the present invention enables the establishment of the human stem cell assay system. Here, stem cells include, in addition to hematopoietic stem cells, stem cells not derived from the hematopoietic system, such as neural stem cells etc. Human stem cells are identified by the existence of a cell surface marker which relates to a specific epitope site identified by an antibody, and for example, they can be isolated as CD34 positive cells from e.g. human bone marrow, umbilical cord blood, peripheral blood etc.

Stem cells are suspended in a solution such as physiological saline, phosphate buffered physiological saline etc., which exerts no influence on cells and living organisms, and $1 \times 10^4$ to $1 \times 10^6$ of cells are intravenously administered into the mouse, thereby carrying out the transplantation.

Cells are collected, several weeks after transplanting, from each organ such as peripheral blood, the spleen, bone marrow, the thymus etc. of the mouse to which the cells have been transplanted. The surface antigens of these cells are examined using e.g. FACS (Fluorescence-activated cell sorter), and thereby the differentiation of the transplanted cells is examined. In this case, examples of cell surface antigen markers to be used as index include: CD34 which relates to stem cells; CD3, CD4, CD8 etc. which relate to T-cells; CD10, CD19, CD20 etc. which relate to B-cells; CD5 etc. which relate to $B_1a$ cells; CD33 etc. which relate to myeloid cells; CD11c etc. which relate to dendritic cells; CD45 etc. which relate to the whole leukocytes; CD11a, CD11b etc. which relate to macrophages; CD56 etc. which relate to NK cells; CD38 etc. which relate to plasma cells; CD41 etc. which relate to platelets; and glycophorin A etc. which relate to erythrocytes. According to need, various related markers can be selected.

The production of cytokines such as interferon, interleukin, TNFα etc. in the collected cells, is measured by ELISA etc., and thereby the differentiation of the stem cells is examined.

Further, it is possible to conduct successive transplantations of human stem cells using the mouse of the present invention. That is, true self-replicable human stem cells can be obtained. Specifically, human stem cells are transplanted in the mouse of the present invention, after several weeks undifferentiated human stem cells are collected from bone marrow of the mouse, and further the collected stem cells are transplanted in the mouse of the present invention. By repeating the transplantation and collection, human stem cells which are free from other cells and have high purity can be obtained in large quantities. By the successive transplantations, human stem cells with at least 99% or more purity, preferably 99.7% or more purity can be obtained. Conventional mice allow up to secondary transplantation, though the mouse of the present invention enables more than two successive transplantations.

For the treatment of leukemia or the like, human stem cells obtained using the mouse of the present invention can be transplanted to humans. Also, the mouse is usable for gene therapy targeting human stem cells by introducing a foreign gene into human stem cells and transplanting them to the mouse of the present invention for proliferation. With the aid of virus vectors such as lentivirus vectors, retrovirus vectors, adenovirus vector, and adeno-associated virus vector, a gene can be introduced into stern cells. Examples of the genes to be used here include an ADA gene for adenosine deaminase deficiency (ADA) patients. After these genes are introduced into human stem cells, the cells are transplanted to the mouse of the present invention for proliferation and purification and then administered to patients, thereby enabling gene therapy.

3. Production of Human Antibodies Using the Mouse of the Present Invention

Using the mouse of the present invention, established human cell lines which produce human antibodies, and human antibodies can be obtained. The above-described stem cells are transplanted to the mouse of the present invention, and cells responsible for immunity such as T-cells or B-cells are differentiated and proliferated. Alternatively, cells responsible for immunity such as human T-cells or B-cells are transplanted to the mouse and engrafted in the mouse body, and thereby obtained is a mouse having the cells responsible for human immunity and capable of producing human antibodies. When human stem cells are transplanted, the differentiation and proliferation of T-cells and B-cells are realized in 6 to 8 weeks, enabling the production of human antibodies.

By administering antigens to the mouse having human T-cells and B-cells engrafted thereto and held, it is possible to obtain human antibodies against the antigens and cells capable of producing the antibodies. The administration of the antigens to the mouse of the present invention may be carried out by the same method as is conventionally used for immunizing a mouse.

Human antibody producing cells can be collected from each organ of the mouse, especially the spleen, lymph nodes etc. When the ratio of the human antibody producing cells is high, the collected cells can directly be used for establishing a cell line. However, when the ratio is low, if necessary, purification may be carried out by e.g. the affinity column method using anti human B-cell antibodies. Further, it is desirable to eliminate mixed-in mouse cells by e.g. cytolysis method using anti mouse antibodies and complements.

The thus obtained human antibody producing cells are made into a established line by a transformation method using Epstein-Barr virus (EBV), a cell fusion method wherein the cells are fused with suitable proliferation viable cells, or the like. Then, obtainable is a human antibody-producing established cell line capable of multiple passages while producing antibodies.

4. Production of a Pathologic Model Mouse with Tumor

In the mouse of the present invention, human tumors can be engrafted and proliferated, and an animal model of a human tumor can be obtained by transplanting tumor cells to the mouse of the present invention. For example, the administration of the human tumor cells causes the proliferation thereof inside the mouse body, and thus a mouse having a human tumor can be obtained. Examples of the cells to be used in this case include subcultured lines of human tumor in a conventional nude mouse, and cell lines derived from HTLV-1 leukemia such as ED-40515(−), MT-1 and TL-Om1. In addition, human tumor tissues are chopped into pieces having a size of several mm, and these cancer tissue pieces may directly be transplanted and engrafted to the mouse of the present invention. In this case, the site of the mouse to which tumor cells or tissues are transplanted is not limited, but in the case of cells, they may be transplanted intraperitoneally, intravenously or subcutaneously to the mouse and in the case of the tissues, they may be transplanted subcutaneously to the mouse. Any subcutaneous site of the mouse may be acceptable such as subcutaneous gluteal region, but it is desirable to transplant them subcutaneously at an auricle or a dorsal region because the tumor can be checked without incision. Further, in order to obtain results which reflect clinical effects of an anti cancer agent, it is desirable to transplant them at the identical site as that for clinical test (in the case of colon cancer cells, the cells are to be transplanted to the colon). When the cells are transplanted, a tumor is formed within several weeks to several months. Specifically, when HTLV-1 cells are transplanted subcutaneously at a posterior auricle, a tumor is formed in 2 weeks, thereby enabling expeditious production of a practical tumor model mouse.

Moreover, when a tumor is transplanted to the mouse of the present invention, metastases of tumor cells such as leukemic changes are observed and the mouse is usable as a model animal for tumor metastasis.

Using the thus obtained human tumor model mouse, screening of an anti cancer agent, antimetastatic drug etc. can be performed. As a method therefor, a candidate agent is administered to a mouse having a tumor formed, by a suitable method e.g. oral, transdermal administration or the like. Then, observation on the size of the tumor, the size and number of metastatic focuses, the viability of the mouse etc., allows judgment on the effect of the drug.

5. Production of a Viral Infectious Disease Model Mouse

Use of the mouse of the present invention enables the obtainment of a viral infectious disease model mouse. Namely, by transplanting to the mouse of the present invention cells which may be infected with a human virus, and infecting the cells with the virus, or transplanting cells infected with a virus, it is possible to obtain a viral infectious disease model animal, which has virus-infected cells engrafted and held.

In a conventional mouse, only an M-tropic virus which infects macrophages can proliferate, but the proliferation of T-tropic viruses such as HIV, HTLV-1, which infects T-cells becomes possible using the mouse of the present invention.

For example, $1\times10^7$ to $1\times10^8$ of human peripheral blood mononuclear leukocytes are intraperitoneally administered to the mouse of the present invention, and after several days some hundreds to thousands of $TCID_{50}$ of HIV were inoculated, thereby obtaining a HIV-infected model mouse having human cells infected with HIV. The HIV infection can be detected through the expression of HIV antigens such as p24 positive cells as an index.

Instead of HIV, the inoculation of HTLV-1 enables the obtainment of an HTLV-1 infected model mouse.

Use of the animal model for disease obtained according to the present invention, allows in vivo research on proliferation mechanisms of HIV, HTLV-1 etc., further development of therapies for virus infections, screening of therapeutic products for virus infection, or the like.

6. Production of a Mouse Having Enhanced Engraftment Capacity of Heterologous Cells Using a NOG Mouse Use of the NOG mouse of the present invention enables the production of a mouse having more enhanced heterologous cell engraftment. For example, such a mouse can be obtained by backcrossing a mouse wherein a gene relating to the mouse immune system is knocked out with the NOG mouse of the present invention. Examples of the genes relating to the immune system include cytokine receptor gene, cytokine gene etc.

Further, by introduction of human cytokine gene, which relates to the differentiation and proliferation of human cells, or the like (e.g. hGM-CSF or hSCF etc.), it is possible to produce a mouse having more enhanced heterologous cell engraftment. For instance, in accordance with a method of Pro. Natl. Acad. Sci. USA 77:7380–7384, 1980, or the like, the above gene is inserted into a pronuclear fertilized egg of the mouse, and an individual having this introduced gene incorporated thereinto is selected, thereby producing a mouse which expresses a human cytokine gene etc. Then, this mouse and the NOG mouse of the present invention were crossed with each other, thereby producing a mouse having enhanced heterologous cell engraftment.

BRIEF DESCRIPTION OF THE DRAWINGS

FIGS. 2A and 2B show time-course changes of human CD45 positive cells and human CD41 positive cells, after the introduction thereof, in peripheral blood of the NOG mouse to which CD34 positive cells are transplanted.

FIGS. 9A and 9B show engraftment and differentiation of human cells in the thymus of the OG mouse to which human CD34 positive cells have been introduced.

BEST MODE FOR CARRYING OUT THE INVENTION

Figure 1:
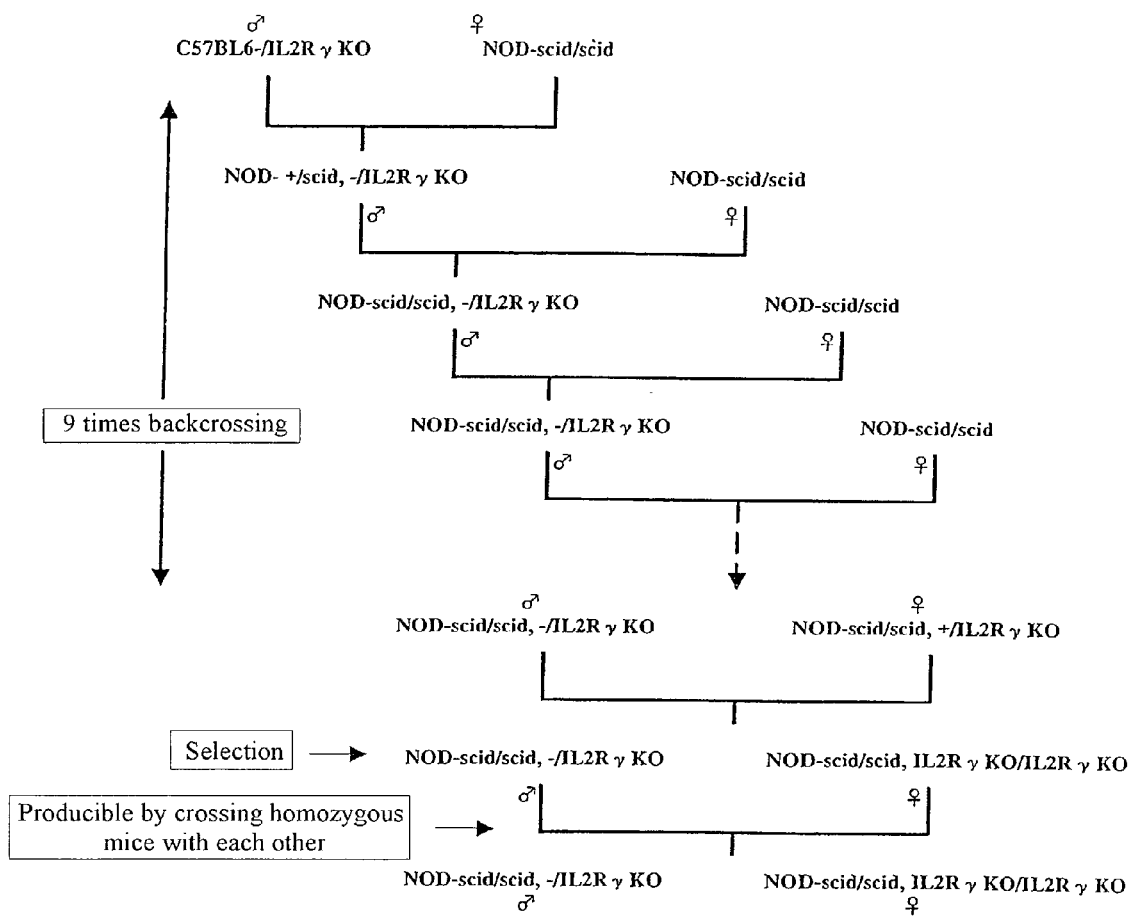
FIG. 1 shows an outline of backcrossing for producing a NOG mouse.

Next, the present invention will be described in detail by referring to Examples.

EXAMPLE 1

Production of an Immunodeficient Mouse (NOG Mouse) with the Deletion of NK Activity and Declined Dendritic Cell Function, Examination of the Heterologous Cell Engraftment in the Mouse, and Establishment of an Assay System of Human Stem Cells Using the Mouse (1) Production of an Immunodeficient Mouse (NOG Mouse) With the Elimination of NK Activity and Reduced Dendritic Cell Function In order to obtain multifunctional immunodeficient mice with depleted NK activity, interleukin-2 receptor γ chain knockout mice (IL-2RγKO mice) (8 week-old) which were transferred from Prof. Kazuo Sugamura (Department of Microbiology and Immunology, Tohoku University, School of Medicine) were backcrossed with NOD-Shi-scid mice (8 week-old) which were kept in the Central Institute for Experimental Animals (also available from CLEA JAPAN, INC.), and thereby F1 mice having an IL-2Rγ mutant gene introduced thereinto were produced. The introduction of the mutant IL-2Rγ chain gene in the F1 mice was confirmed by PCR amplification and detection of the gene. Specifically, first, DNAs were extracted by a DNA automatic extractor (MagExtractor manufactured by TOYOBO) from 100 μl of blood taken from ocular fundus of the F1 mice. PCR buffer solution containing 23.5 μL of 1.5mM $MgCl_2$, 0.4 mM dNTP and two sets of 25 pmol primers (the following primers PI and PIII were used for the determination of wild type, and a set of the following primers PI and PII were used for the determination of mutant type) was added to 1.5 μL of this DNA, and PCR was conducted under the following amplification conditions for the determination of whether IL-2Rγ chain genes were wild type or mutant type.

(Primers)

```
PI    5'-CTGCTCAGAATGATGCCTCCAATTCC-3'  SEQ ID NO:1

PII   5'-CCTGCGTGCAATCCATCTTGTTCAAT-3'  SEQ ID NO:2

PIII  5'-GATCCAGATTGCCAAGGTGAGTAG-3'    SEQ ID NO:3
```

(PCR Amplification Conditions)

The conditions were heating at 94° C. for 5 minutes; 30 to 35 cycles of 1 minute at 94° C., 1 minute at 55° C., and 1 minute at 72° C.; and thereafter heating at 72° C. for 10 minutes.

The PCR products obtained by the above PCR were subjected to electrophoresis in 2% agarose gel, and measured according to the size of the coloring band detected after ethidium bromide stain. The sizes of the bands, about 660 bp for wild type and about 350 bp for mutant type, were observed.

(Backcrossing)

Next, the F1 mice having the mutant IL-2Rγ gene introduced thereinto were crossed with NOD/Shi-scid mice, thereby obtaining F2 mice. Further, by detecting the introduction of the mutant IL-2R γ chain gene into the F2 mice in the same manner as above, and detecting immunoglobulins in serum by an immunodiffusion method, mouse individuals which had the mutant IL-2R γ chain gene and had a homozygous scid gene were selected. Thereafter, the mouse individuals were crossed with NOD/Shi-scid mice, and among the born mice, mice having mutant IL-2R γ chain gene were further crossed with NOD/Shi-scid mice.

The above backcross was repeated at least 9 times, thereby producing NOG (NOG) mice (FIG. 1 shows the outline). Here, since the IL-2R γ chain gene exists on an X chain chromosome, it is effective to use male IL-2RγKO mice.

(2) Examination on Engraftment Capacity of Heterologous Cells in NOG Mice

Next, using the NOG mice obtained by the above crossing and conventional immunodeficient mice, NOD/Shi-scid mice, examinations were made on the level of impact that anti-NK antibody treatment has on engraftment of heterologous cells in these mice.

(Anti-IL-2 Receptor β Chain Monoclonal Antibody)

Anti-IL-2 receptor β chain monoclonal antibodies (clone TM β1) were produced from hybridomas produced and provided by Prof. Masayuki Miyasaka, School of Medicine, Osaka University (Tanaka T, Tsudo M, Karasuyama H et al., A novel monoclonal antibody against murine IL-2Receptor beta-chain. Characterization on of receptor expression in normal lymphoid cells and EL-4 cells. J Immunol 1991;147 (7):2222–8). In particular, the hybridomas were intraperitoneally administered to BALB/cA-nu mice and collected from ascites after several weeks.

One mg per mouse of the antibodies was intraperitoneally administered to five NOD/Shi-scid mice (8 to 12 week-old) and three NOG mice (8 to 12 week-old). Further, as controls with no administration of the antibodies, physiological saline was administered to four NOG mice (8 to 12 week-old).

Moreover, human peripheral blood lymphocytes were collected by use of density gradient centrifugation using Lymphoprep, from blood taken from volunteers.

$1 \times 10^7$ of the obtained human peripheral blood mononuclear leukocytes were intraperitoneally administered to the above mice on the second day after the administration of TM β1.

The mice were sacrificed 2 weeks after the administration of human peripheral blood lymphocytes, and the ascites containing the whole peritoneal exudates cells were fully washed with RPMI-1640 culture medium and thereby collected. Out of all the peritoneal cells, all the peritoneal exudates cells were counted by flow cytometry, and depending on their amounts, the engraftment and proliferation of human cells into mice were determined. The same operations were conducted for control mice with no administration of the antibodies. Their results are shown in Table 1.

First, 2.4 Gy of X ray were irradiated on NOG mice (8 to 12 week-old) and NOD/Shi-scid mice (8 to 12 week-old) which were numbered as indicated in Table 2. Then, 20 μL per mouse of anti asialo-GM1 antibodies diluted with 400 μL PBS were administered to these mice just before the administration of the cells derived from human umbilical cord blood. Also, physiological saline was intraperitoneally administered to control mice (No. 5, 6, 10, 11, 15, 16 mice in Table 2) without administration of the antibodies.

With respect to human umbilical cord blood CD34 positive cells, mononuclear leukocytes were collected by Ficoll-Hypaque gradient centrifugation from umbilical cord blood taken from volunteers from whom approval was each obtained in advance. Further, CD34 positive cells were isolated by Dynabeads M-450 CD34 and DETACHaBEAD CD34 (Dynal As, Oslo, Norway). (Ueda T, Tsuji K, Yoshino H et al., Expansion of human NOD/SCID-repopulating cells by stem cell factor, Flk2/Flt3 ligand, thrombopoietin, IL-6, and soluble IL-6 receptor. J Clin Invest 2000;105(7):1013–21)

$1 \times 10^5$ of the obtained CD34 positive cells derived from human umbilical cord blood were introduced through tail

TABLE 1

Impact of anti-NK antibodies (TMβ1) on engraftment and proliferation of human peripheral blood mononuclear leukocytes in NOD/Shi-scid mice and NOG mice

| Mouse strain | TMβ1 treatment | Number of mice | Number of collected cells ($\times 10^6$, distribution) | HLA+ (distribution) | hCD4+ | hCD8+ |
|---|---|---|---|---|---|---|
| NOD/Shi-scid | + | 5 | 4.8 (2.77–6.8) | 41.1 (4.2–65) | ND | ND |
| NOG | + | 3 | 11.1 (8.3–15.0) | 61.9 (47.4–74.6) | 19.8 | 28.2 |
| | − | 4 | 11.2 (7.9–20) | 63.3 (51.4–69.7) | 34.3 | 25.9 |

It is clear from the results shown in Table 1 that extremely high ratios of human cells were differentiated, engrafted and proliferated, even without the treatment of the antibodies, in NOG mice to which human peripheral blood mononuclear leukocytes were introduced, as compared with conventional TM β1 treated mice.

(Anti Asialo-GM1 Antibody)

Next, using NOG mice and NOD/Shi-scid mice, examinations were made on the level of impact, which would be given by anti asialo-GM1 antibodies (AGM1) (rabbit) (Wako Pure Chemical Industries, Ltd., 014-09801), on engraftment capacity of cells derived from human umbilical cord blood in these mice.

veins of the mice immediately after the administration of anti asialo-GM1 antibodies.

The mice were sacrificed 4 weeks after the administration of CD34 positive cells derived from human umbilical cord blood, their peripheral blood was collected, and human cells (CD45+) in mononuclear leukocytes and human platelets (CD41+) in the whole blood were counted by flow cytometry. Depending on their amounts, the engraftment capacity and proliferation of human cells into mice were determined. The same operations were conducted for control mice without administration of the antibodies. Their results are shown in Table 2.

TABLE 2

Differentiation and proliferation of introduced human umbilical cord blood CD34+ in NOG mice

| Mouse No. | Mouse strain | AGM1 treatment | No. of introduced CD34+ cells | Days after transplant | No. of leukocytes ($10^2$/ul) | No. of erythrocytes ($10^4$/ul) | No. of platelets ($10^4$/ul) | hCD45+ (%) | hDC45+ (/ul) | hCD41+ (%) | hCD41+ (/ul) |
|---|---|---|---|---|---|---|---|---|---|---|---|
| 1 | NOD/Shi-scid | + | 100000 | 31 (4 wk) | 12 | 782 | 134 | 0.19 | 2 | 0.001 | 20 |
| 2 | NOD/Shi-scid | + | 100000 | 31 (4 wk) | 12 | 809 | 147 | 0.94 | 11 | 0.022 | 318 |
| 3 | NOD/Shi-scid | − | 100000 | 31 (4 wk) | 10 | 758 | 104 | 0.48 | 5 | 0.004 | 41 |

TABLE 2-continued

Differentiation and proliferation of introduced human umbilical cord blood CD34+ in NOG mice

| | | | No. of | | 4 weeks after introduction | | | | | | |
|---|---|---|---|---|---|---|---|---|---|---|---|
| Mouse No. | Mouse strain | AGM1 treatment | introduced CD34+ cells | Days after transplant | No. of leukocytes ($10^2$/ul) | No. of erythrocytes ($10^4$/ul) | No. of platelets ($10^4$/ul) | hCD45+ (%) | hDC45+ (/ul) | hCD41+ (%) | hCD41+ (/ul) |
| 4 | NOD/Shi-scid | − | 100000 | 31 (4 wk) | 14 | 773 | 109 | 3.24 | 45 | 0.166 | 1814 |
| 5 | NOG | − | 100000 | 31 (4 wk) | 12 | 713 | 89.3 | 5.84 | 70 | 0.255 | 2274 |
| 6 | NOG | − | 100000 | 31 (4 wk) | 17 | 749 | 108 | 9.29 | 158 | 0.324 | 3498 |
| 7 | NOD/Shi-scid | + | 100000 | 29 (4 wk) | 10 | 734 | 139 | 1.82 | 18 | 0.056 | 772 |
| 8 | NOD/Shi-scid | + | 100000 | 29 (4 wk) | 10 | 787 | 118 | 1.51 | 15 | 0.094 | 1105 |
| 9 | NOD/Shi-scid | − | 100000 | 29 (4 wk) | 7 | 722 | 132 | 0.97 | 7 | 0.059 | 776 |
| 10 | NOG | − | 100000 | 29 (4 wk) | 36 | 602 | 218.1 | 1.84 | 66 | 0.170 | 3709 |
| 11 | NOG | − | 100000 | 29 (4 wk) | 10 | 725 | 111 | 9.28 | 93 | 0.518 | 5748 |
| 12 | NOD/Shi-scid | + | 100000 | 28 (4 wk) | 7 | 696 | 92.4 | 1.74 | 12 | 0.007 | 63 |
| 13 | NOD/Shi-scid | + | 100000 | 28 (4 wk) | 10 | 787 | 96 | 0.40 | 4 | 0.008 | 73 |
| 14 | NOD/Shi-scid | − | 100000 | 28 (4 wk) | 10 | 710 | 82.6 | 0.41 | 4 | 0.021 | 173 |
| 15 | NOG | − | 100000 | 28 (4 wk) | 2 | 684 | 103 | 8.52 | 17 | 0.101 | 1040 |
| 16 | NOG | − | 100000 | 28 (4 wk) | 2 | 773 | 86.5 | 14.98 | 30 | 0.196 | 1692 |
| | | | | Average | NOD/Shi-scid (AGM1+) | | | 1.10 | 10.52 | 0.03 | 391.74 |
| | | | | | NOD/Shi-scid (AGM1−) | | | 1.27 | 15.25 | 0.06 | 701.14 |
| | | | | | NOG | | | 7.11 | 61.99 | 0.22 | 2565.96 |

It is clear from the results shown in Table 2 that extremely high ratios of human cells were differentiated, engrafted and proliferated, even without the treatment of the antibodies, in NOG mice to which CD34 positive cells derived from human umbilical cord blood were introduced, as compared with conventional mice which were treated with anti asialo-GM1 antibody.

(3) Establishment of Assay System of Human Stem Cells Using NOG Mice

Mice to be used here were NOD/Shi-scid mice and NOG mice of the present invention. $1 \times 10^5$ of CD34 positive cells taken from human umbilical cord blood (CB) were transplanted to the above mice which had received 2.4 Gy of radiation.

Human cells in peripheral blood, bone marrow, spleens, and thymuses were analyzed by FACS. The ratios of CD45 positive cells in peripheral blood 8 weeks after the transplant were 37% for NOG mice and 7% for NOD/Shi-scid mice. In bone marrow, the ratios were 65% and 20%, respectively. In addition to a high ratio of chimerism, it was found that differentiations occurred into various cell lines including B and T lymphocytes in peripheral blood, bone marrow, spleens, and thymuses of the NOG mice 3 month after the transplant. It was observed that human CD33+ bone marrow cells, CD19+B cells, CD3+T cells, CD56+NK cells, CD41a+ huge nucleoplasm, and glycophorin A+ erythrocytes were present in bone marrow. Further, it is interesting to note that though there were observed a small number of human T cells in the thymuses, CD4+/CD8− T cells, CD4−/CD8+ T cells, and CD4+/CD8+ T cells were observed in the spleens. This indicates that human hematopoietic stem cells are differentiated and proliferated into mature T cells at sites apart from the thymus.

Umbilical cord blood was obtained at birth of a healthy newborn from a normal pregnant mother from whom approval was obtained in advance. The umbilical cord blood was heparinized and preserved, and treated by the operation described below within 24 hours after collecting. Then, it was used for a transplant test.

The purification of CD34 positive cells was conducted as follows. The heparinized umbilical cord blood was diluted two times with a buffer solution prepared by mixing phosphate buffered saline with 5% fetal bovine serum, and thereafter mononuclear leukocytes were isolated using Ficoll. From the isolated mononuclear leukocytes, CD34 positive cells were purified by use of Dynabeads™ M-450 CD34 available from Dynal Biotech, Ltd. Although the method therefor is as instructed by Dynal Biotech, Ltd., it is summarized as follows. Using phosphate buffered physiological saline containing 2% bovine serum albumin and sodium citrate, the concentration of the mononuclear leukocytes was adjusted so as to be $4 \times 10^7$/mL. 100 μL of well-suspended Dynabeads CD34 was added per 1 mL of mononuclear leukocyte suspension, and they were blended and reacted with each other over ice for 30 minutes. Beads which formed rosettes with cells were collected using a magnet. Subsequently, to the Beads forming rosettes with cells, a required amount of Detachabead™ CD34 was added and reacted therewith, blending at 37° C. for 15 minutes. As CD34 positive cells were liberated from the Beads, a magnet was used to remove only the Beads, thereby obtaining CD34 positive cells.

For transplanting, 8 to 12 week-old NOD/Shi-scid mice, NOG mice, and NOD/LtSz-scid, β2m null mice, all raised in an SPF (specific pathogen free) environment were used. These mice were raised in the animal experiment facility of Kyoto University, School of Medicine under the regulations of the facility.

In a comparative test for the former 2 types of mice, the mice were twice irradiated with 1.2 Gy gamma ray (gamma cell $^{137}$Cs), and 100,000 of CD34 positive cells per mouse were transplanted through the tail vein. For the NOD/Shi-scid mice, 200 μg of anti asialo GM1 antibodies (Wako Pure Chemical Industries, Ltd.) were intraperitoneally administered immediately before the transplant and every eleventh day after the transplant.

In a comparative test between NOG mice and NOD/LtSz-scid, β2m null mice, the mice were twice irradiated with 1.2 Gy gamma ray in the same way as above, and thereafter 40,000 or 10,000 of CD34 positive cells were transplanted through the tail vein.

After transplantation, 732 mg/L of neomycin sulfate were added to the mice's drinking water for protection against infection.

The mice were ether-anaesthetized at moments as indicated, and then peripheral blood was collected from the orbital venous plexus for measuring the positive ratio of human hemocytes by use of flow cytometry. Although the flow cytometry was conducted in accordance with a widely-used general method, it is summarized as follows. The collected blood was instantly blended well with EDTA-2Na and allowed to stand at room temperature until analysis. An optimum amount of antibodies was added to and reacted with 50 to 100 μL of the whole blood at 4° C. for 30 minutes. Thereafter, hemolysis and immobilization were effected using FACS solution (Becton Dickinson and Co.), and the ratio was measured using FACS Calibur (Becton Dickinson and Co.). In the case of bone marrow and spleen, the mice were sacrificed with cervical vertebra dislocation and femora and spleens were eviscerated. Then, bone marrow and splenic cells were each liberated in culture solution containing 5% fetal bovine serum, and thereafter as cell suspensions, they were treated in the same manner as peripheral blood and analyzed by flow cytometry.

Antibodies to be used for the analysis were FITC conjugated anti human CD45 antibodies, PE conjugated anti human CD10 antibodies, PE conjugated anti human CD33 antibodies, PE conjugated anti human CD3 antibodies, PE conjugated anti human CD34 antibodies, PE conjugated anti human CD41 antibodies (Beckton, Dickinson and Co.), PC5 conjugated anti human CD38 antibodies, PC5 conjugated anti human CD56 antibodies, PC5 conjugated anti human CD19 antibodies (Immunotech), APC conjugated anti mouse CD45 antibodies, and FITC conjugated anti mouse CD41 antibodies (BD Pharmingen).

Figure 2B:
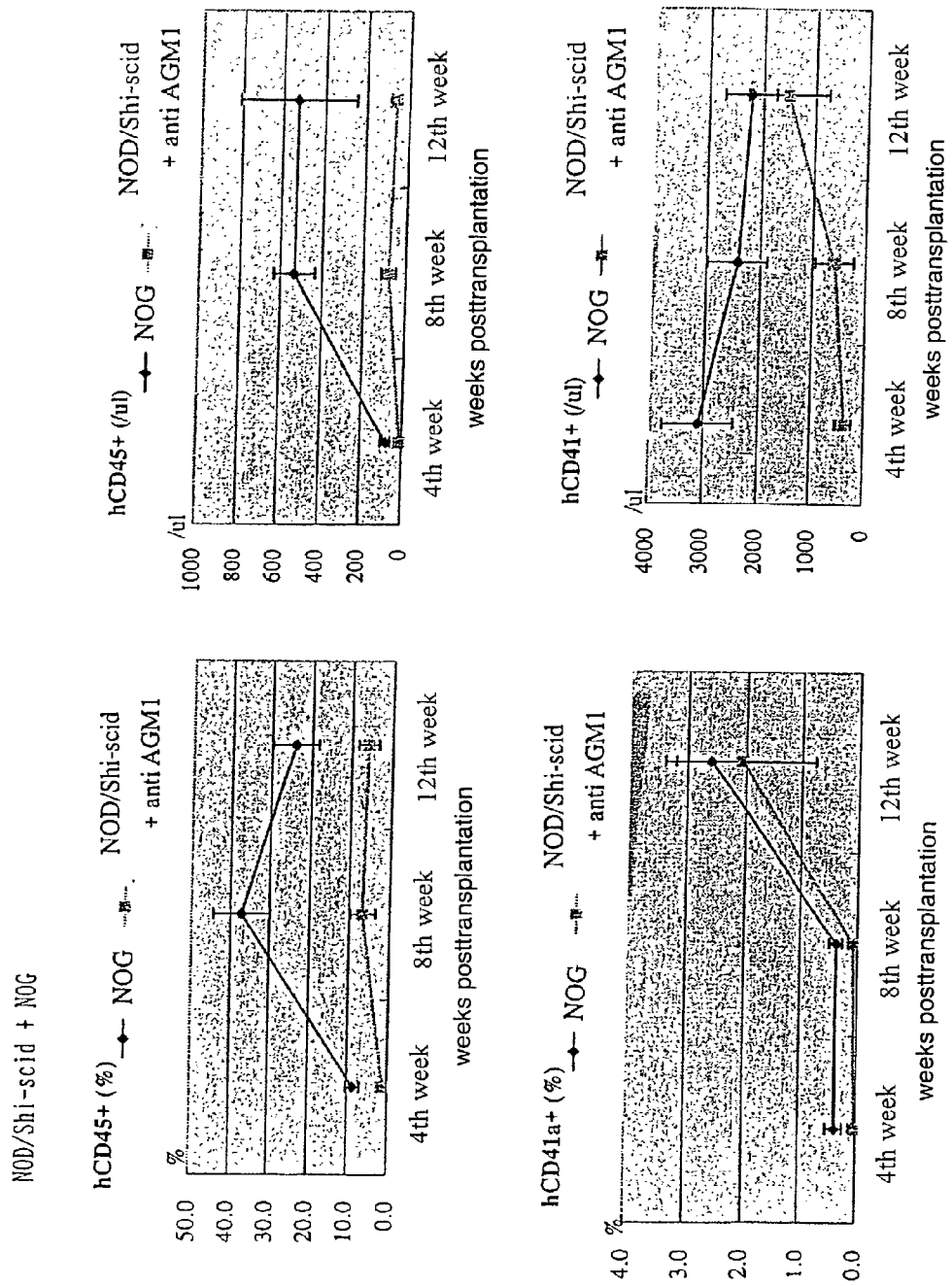
Figure 3:
FIG. 3 shows the ratio of CD45 positive cells in the bone marrow and spleen of the NOG mouse to which CD34 positive cells are transplanted.

With respect to human CD45 positive cells and human CD41 positive cells in mouse peripheral blood, changes in the ratios (%) and the absolute numbers (/μL) were investigated every fourth week until the 12th week (FIG. 2A and FIG. 2B). As shown in FIGS. 2A and 2B, significantly high ratios and absolute numbers were observed for NOG mice. The mice were sacrificed from 12 weeks onward after the transplant, and when the ratios of human CD45 positive cells in bone marrow and spleens were investigated in the same way as above, the NOG mice had very high positive ratios. (FIG. 3)

Figure 4:
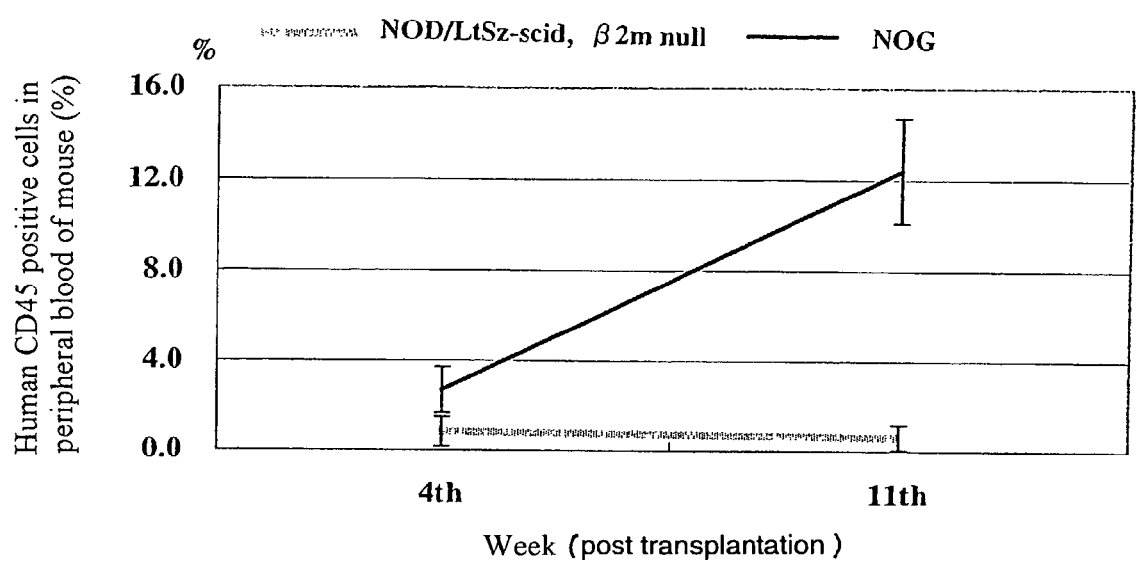
FIG. 4 shows the ratios of CD45 positive cells in peripheral blood of mice in a comparative test between the NOG mouse and a β2 microglobulin deficient NOD-SCID mouse (NOD/LtSz-scid, β 2 m null mouse).

In the comparative test between NOG mice and NOD/LtSz-scid, β2m null mice, the positive ratios of human CD45 positive cells in mouse peripheral blood were investigated (FIG. 4). As shown in FIG. 4, the NOG mice had a higher positive ratio of human cells and exhibited a better engraftment capacity of human cells than NOD/LtSz-scid, β2m null mice.

EXAMPLE 2

Examinations on Functional Incompetence of Dendritic Cells of NOG Mice in NK Activity and Cytokine Production Three female NOG mice (10 to 12 week-old) of the present invention, four female and four male NOD/Shi-scid mice (10 to 12 week-old) obtained by backcrossing C.B-17-scid mice with NOD/Shi mice, and two female and two male NOD/LtSz-scid, β2m null mice (10 to 12 week-old) (or referred to as null β 2m(null)NOD/LtSz-SCID, β2m microglobulin deficient NOD/SCID mice; produced by Dr. Shultz, L. D. et al. of The Jackson Laboratory Kollet O, Peled A, Byk T et al., beta2 microglobulin-deficient (β2m(null)NOD/SHI-SCID mice are excellent recipients for studying human stem cell function. Blood 2000;95(10):3102–5) were used for the following examinations.

After the NOD/Shi-scid mice were treated with anti asialo GM1 antibodies (αAGM), spleen cells were collected. The obtained cells were divided into two groups, and CD11c antigen positive cells (regarded as dendritic cells) were removed from one of them using a magnetic cell sorter (MACS). Likewise, splenic cells were collected from non-treated NOD/LtSz-scid, β2m null mice and NOG mice. A small amount of these cells was taken from each of them and provided for FACS analysis. Further, these four kinds of cells were divided into three groups: group I: NOG mice (3 mice); group II: αAGM non-treated NOD/Shi-scid mice (2 males), αAGM treated NOD/Shi-scid mice (3 mice), and NOD/Shi-scid mice (3mice) which were treated with αAGM and further from which CD11c were removed; and group III: NOD/LtSz-scid, β2m null mice (4 mice). They were adjusted to have a cell concentration of $1 \times 10^7$/ml in RPMI-1640, and 100 μl of each of them were dispensed into a well, stimulated by an equivalent amount of Listeria monocytogenes (LM) antigens, and cultured (using Triplicate). Since LM is $10^{11}$ Units/mL, it was diluted for use so as to be $2 \times 10^7$ Units/mL with RPMI-1640. In this case, specimens with no LM addition were used as a control. After 24 hours, the supernatants were collected, and the amounts of cytokine such as IFN-γ were determined by ELISA.

Subclasses (in particular, CD11c, CD11b) in spleen cells were analyzed by FACS.

FITC-labeled CD3 and biotine-labeled Pan NK(DX5) were used as a T-cell marker and an NK cell marker, respectively. FITC-labeled anti-CD11c and PE-labeled anti-CD11b were used as a macrophage and dendritic cell marker.

Further, NK activity in NOG, C.B-17-scid, NOD/Shi-scid, and NOD/LtSz-scid, βm null mice (10 to 12 week-old) was examined by cytotoxicity test targeting $^{51}$Cr-labeled NK susceptible YAC-1 cells. Namely, splenic cells were isolated from the mice and mixed and cultured with $^{51}$Cr-labeled YAC-1 cells at various ratios therebetween. After culturing at 37° C. for 4 hours under 5% $CO_2$, the radioactivity in supernatants was measured by a liquid scintillation counter. The NK activity is indicated according to the following calculation method.

% specific cytotoxicity=(specific radioactivity−background radioactivity)/(maximum radioactivity−background radioactivity)×100

Figure 5A:
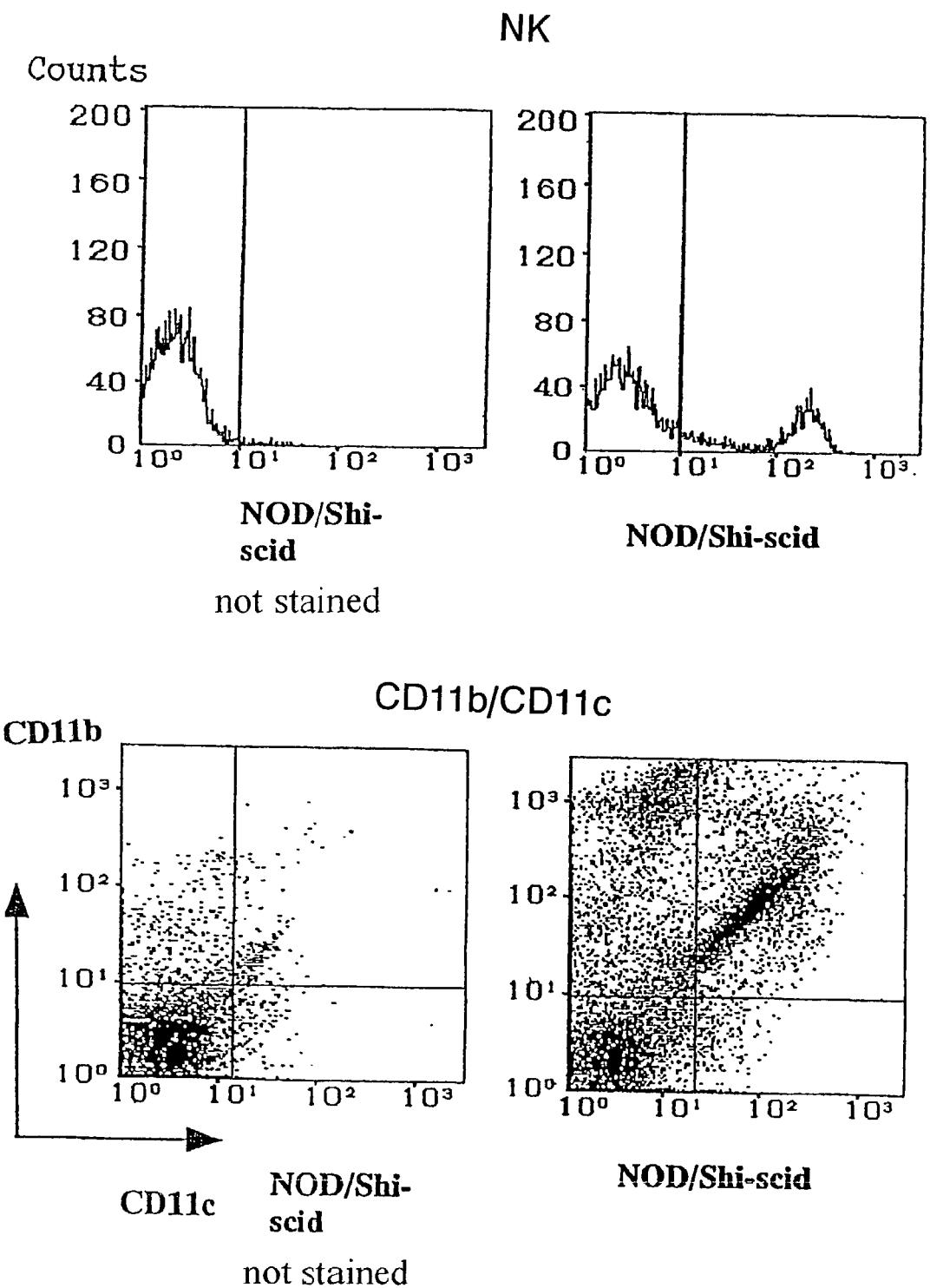
FIGS. 5A and 5B show FACS patterns of NK cells and dendritic cells in spleen cells obtained from each mouse strain.
Figure 5B:
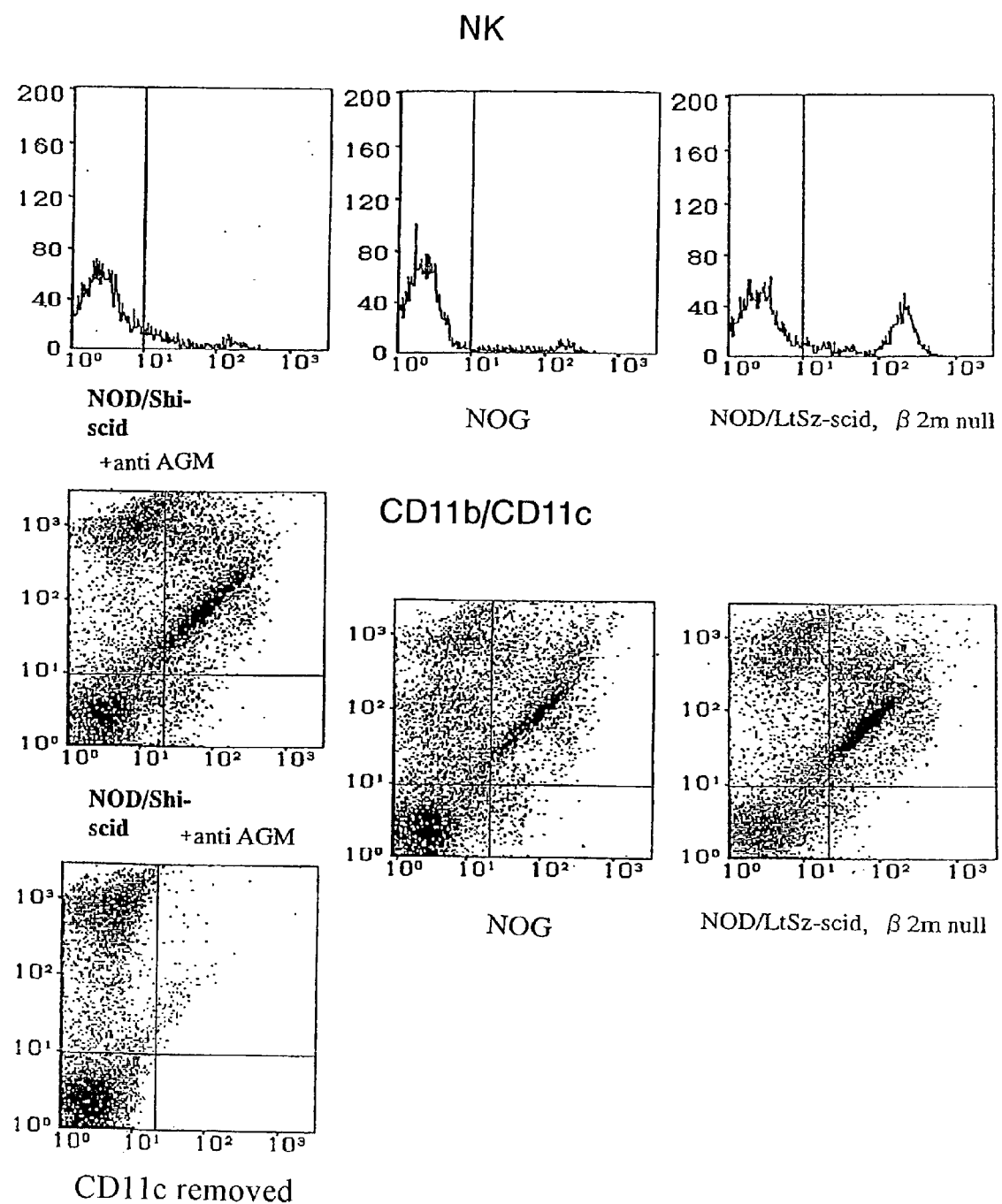

FIGS. 5A and 5B show FACS patterns of the spleen cells obtained from each mouse strain.

NK cells were detected from NOD/Shi-scid and NOD/LtSz-scid, β2m null mice, though NK cells were not detected at all from NOD/Shi-scid mice not treated with anti asialo GM1 antibody and NOG mice. CD11c positive cells which were used as a dendritic cell marker were detected from all the mice at extremely high ratios. It was confirmed that CD11c positive cells were almost completely removed from the splenic cells of the NOD/Shi-scid mice not treated with anti asialo GM1 antibody by magnetic beads.

Figure 6A:
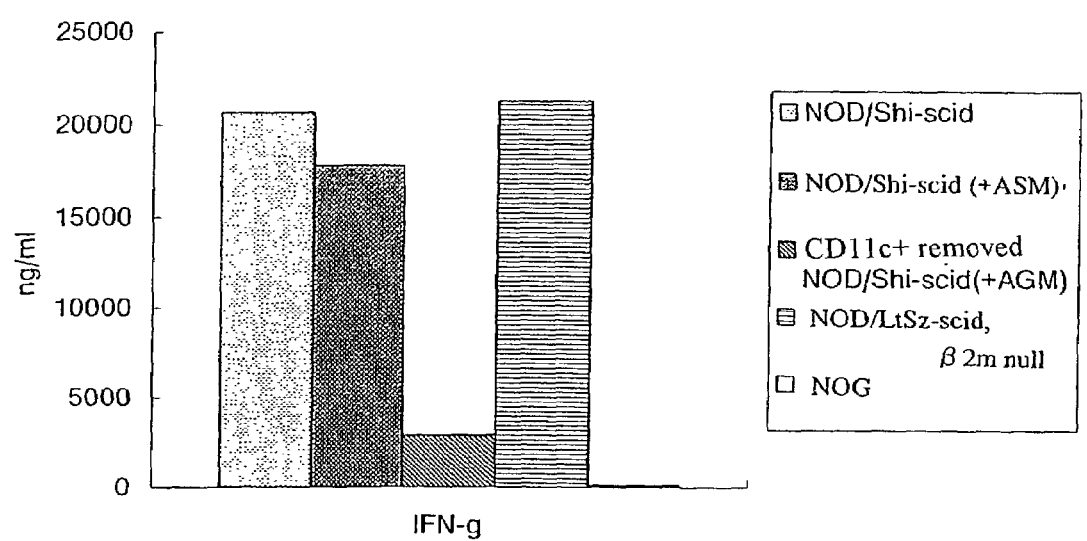
FIGS. 6A, B and C show the results of ELISA for detecting the production amount of cytokine under the stimulation of Listeria monocytogenes antigens in spleen cells obtained from each mouse strain.
Figure 6B:
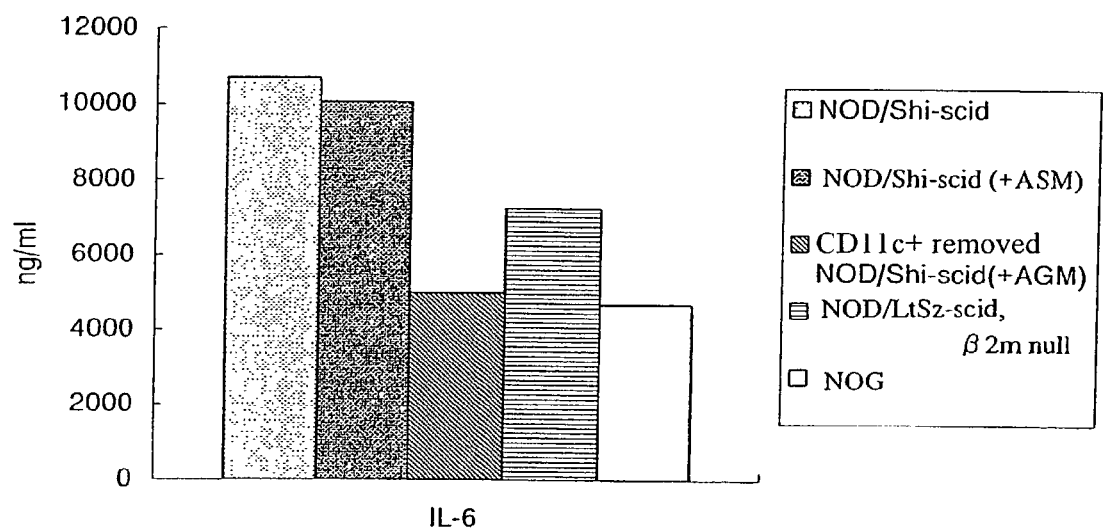
Figure 6C:
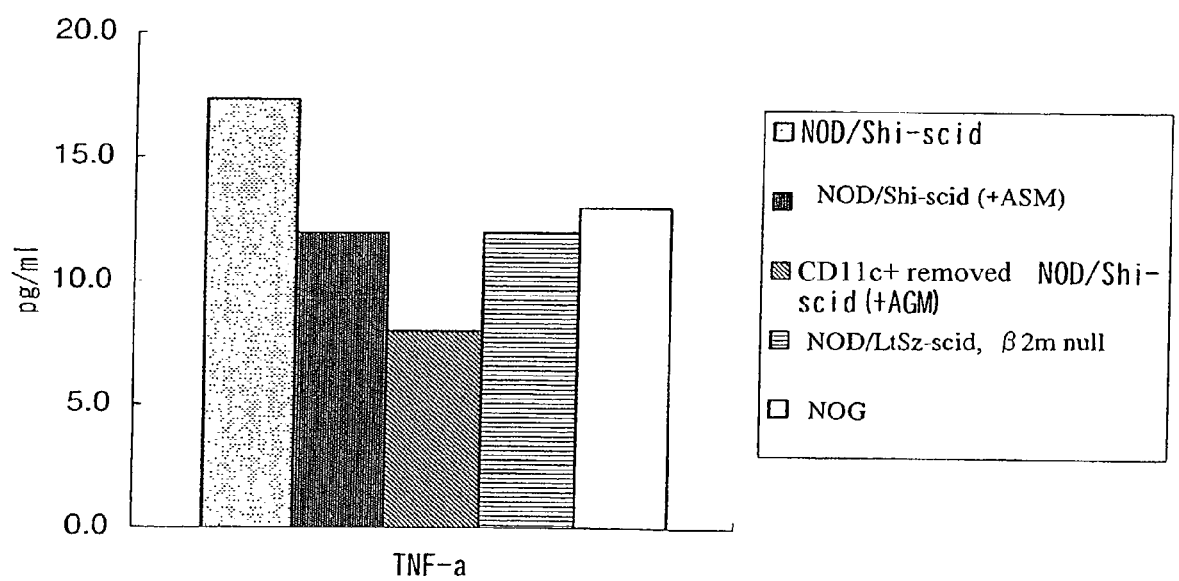

FIGS. 6A, 6B and 6C show detection results by ELISA on the production amount of cytokine in the above splenic cells under the LM stimulation. The following was found: although IFN γ production was observed in NOD/Shi-scid mice not treated with anti asialo GM1 antibody and NOD/LtSz-scid, β2m null mice, there was no detection from NOG mice; and, as with NOG mice, by removing CD11c positive cells from the NOD/Shi-scid mice treated with anti asialo GM1 antibody, IFN γ production was not observed.

Figure 7:
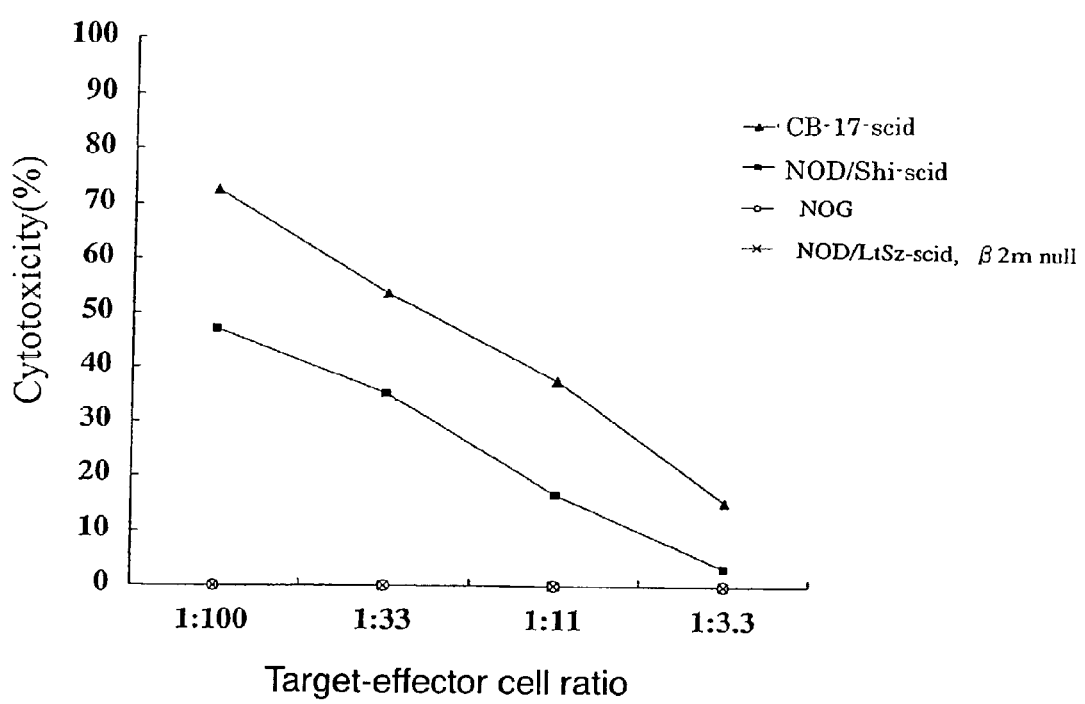
FIG. 7 shows the removal of NK activity in the NOG mouse and the NOD/LtSz-scid, β 2m null mouse.

FIG. 7 shows NK activity of the splenic cells obtained from each mouse strain.

In comparison with C.B-17-scid mice, reduction of NK activity in NOD/Shi-scid mice was observed, but absolutely no NK activity was observed in NOG mice and NOD/LtSz-scid, β2m null mice.

In view of the foregoing, it became clear that NOG mice and NOD/LtSz-scid, β2m null mice completely lost their NK activity. However, according to the result of FACS analysis, it became clear that the NOG mice lost NK cells, though the NOD/LtSz-scid, β2m null mice had NK cells present therein but lost NK activity.

Further, it was revealed that the functional incompetence of the dendritic cells was a cause for the cytokine production decline in splenic cells, which was observed in the NOG mice. On the other hand, it was indicated that the NOD/LtSz-scid, β2m null mice had almost the same patterns of FACS and cytokine production as the anti asialo GM1 antibody-treated NOD/Shi-scid mice. It was obvious that the NOD/LtSz-scid, β2m null mice lost NK cells and their dendritic cells were normal.

EXAMPLE 3

Successive Transplant of Human Stem Cells Using NOG Mice

In order to examine self-replicability of gene-introduced human stem cells, umbilical cord blood stem cells were transplanted to NOG mice, and it was examined whether or not secondary or tertiary transplant is possible.

Umbilical cord blood was obtained from pregnant women, with their consent and approval, for use in tests. After mononuclear cells were isolated from umbilical cord blood using Ficoll-Hypaque (Lymphoprep, 1.077±0.001 g/ml; Nycomed, Oslo, Norway), CD34 positive cells were purified using a CD34 positive separation column (MACS, Miltenyi Biotec, Glodbach, Germany). The CD34 positive cells had a purity of 96±3%.

Lentivirus vector pCS-CG was a vector which enables a GFP gene to be expressed by a CMP promoter, and it was provided by Dr. Miyoshi (Immunology, Medical Branch, University of Tsukuba). After umbilical cord blood CD34 positive cells were cultured for 24 hours in serum-free medium StemPro TM-34SFM (Gibco BRL) containing 50 ng/mL of each TPO, SCF and Flk-2/Flt-3 ligand (FL), they were subjected to five-hour infection of recombinant lentivirus CS-CG by MOI30 (Kawada H et al., Exp. Hematol. 27:904–915, 1999). Thereafter, cells were washed and subjected to 5-day extracorporeal amplification culture in the same serum-free medium as above in the presence of murine bone marrow stroma cells HESS-5 (Oki M et al., Exp. Hematol. In press. 2001).

After 7 week-old NOD/Shi-scid mice were subjected to 3 Gy radiation, $3\times10^5$ of gene-introduced cells which were amplified by culture, were introduced through the tail vein. After 6 weeks, surface antigens of murine bone marrow cells were analyzed, and $1\times10^7$ of cells were introduced into irradiated NOG mice (secondary transplant). After 6 weeks, the same analysis was conducted, and $1\times10^7$ of cells were introduced into irradiated NOG mice (tertiary transplant). Further, after 6 weeks, the same analysis was conducted.

The analysis of surface antigens was conducted using FACS Calibur (Becton, Dickinson and Co.). The antibodies used here were FITC-labeled anti human CD45 (T-200), PE-labeled anti human CD2 (39C1.5), CD3(UCHT1), CD4 (SK3), CD14(LeuM3), CD19(4G7), CD20(2H7), CD33 (WM53), CD41(P2), CD56(N901), and glycophorin A (KC16), and all of them were purchased from Becton, Dickinson and Co.

Figure 8:
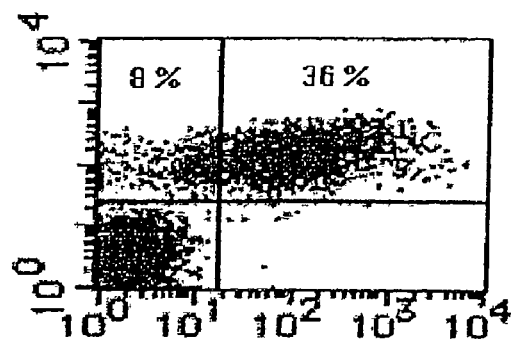
FIG. 8 shows the results of FACS wherein bone marrow cells from primary, secondary and tertiary mice to which human CD34 positive cells have been transplanted, are stained with human CD45.
Figure 8:
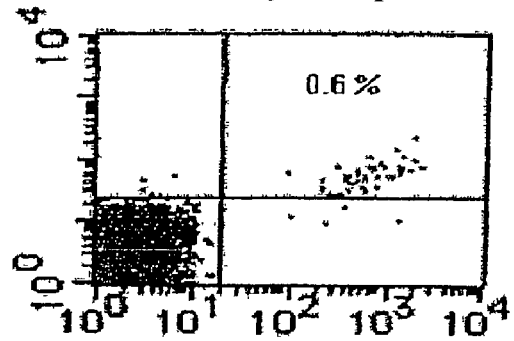
Figure 8:
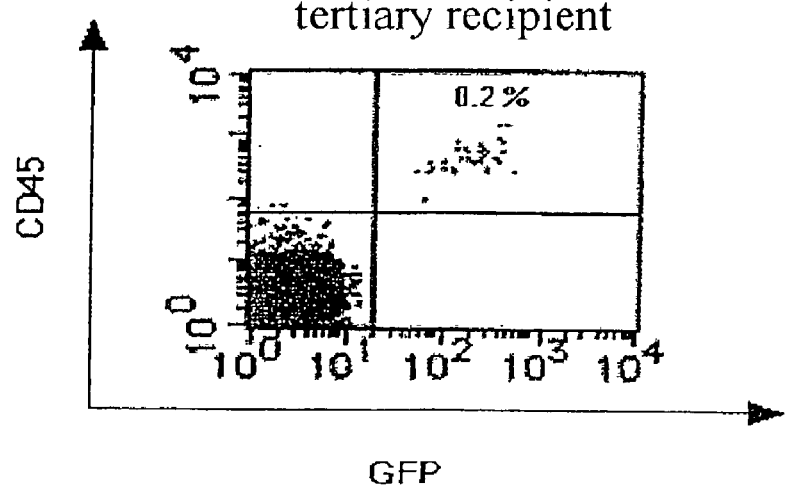
Figure 9B:
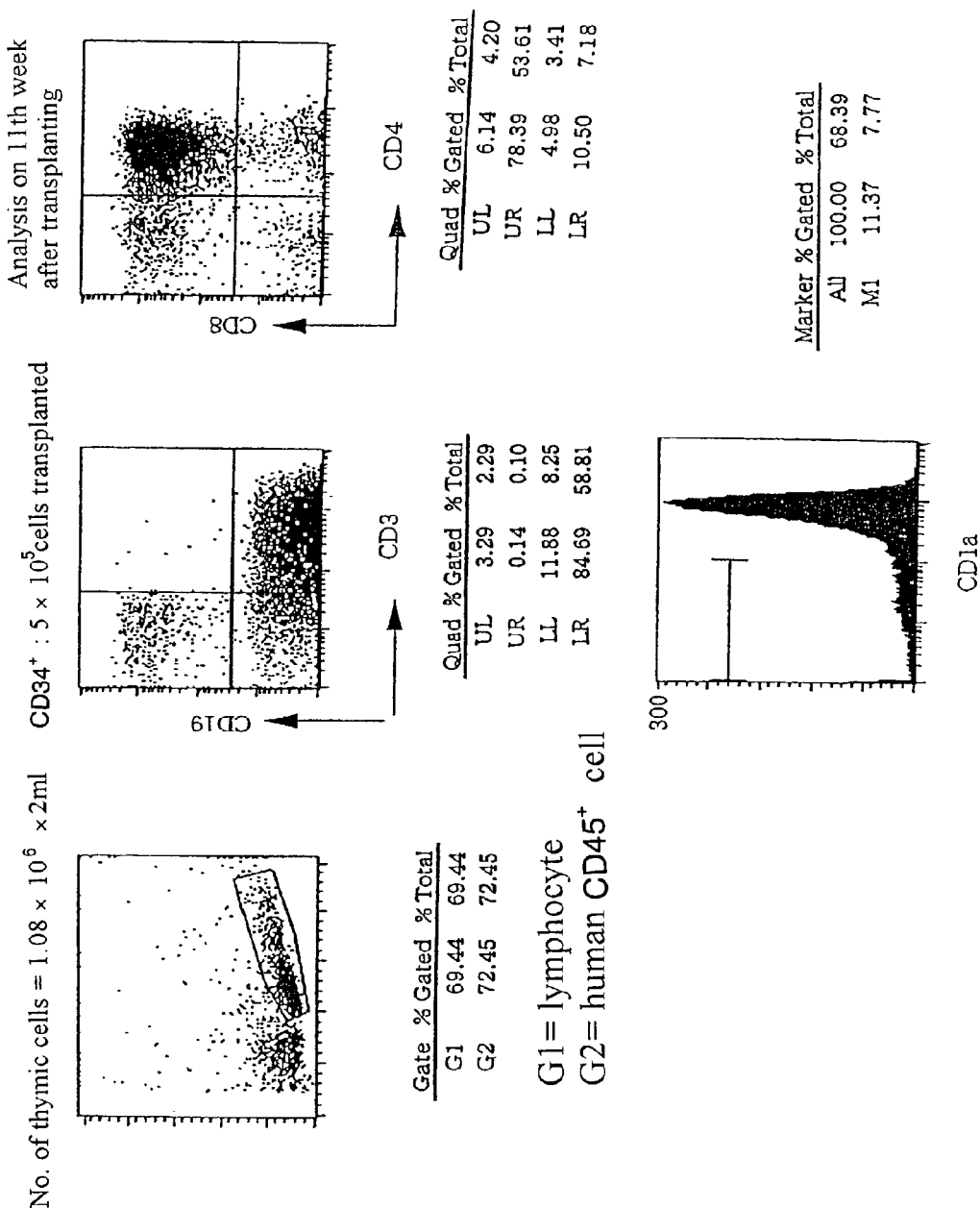
Figure 10A:
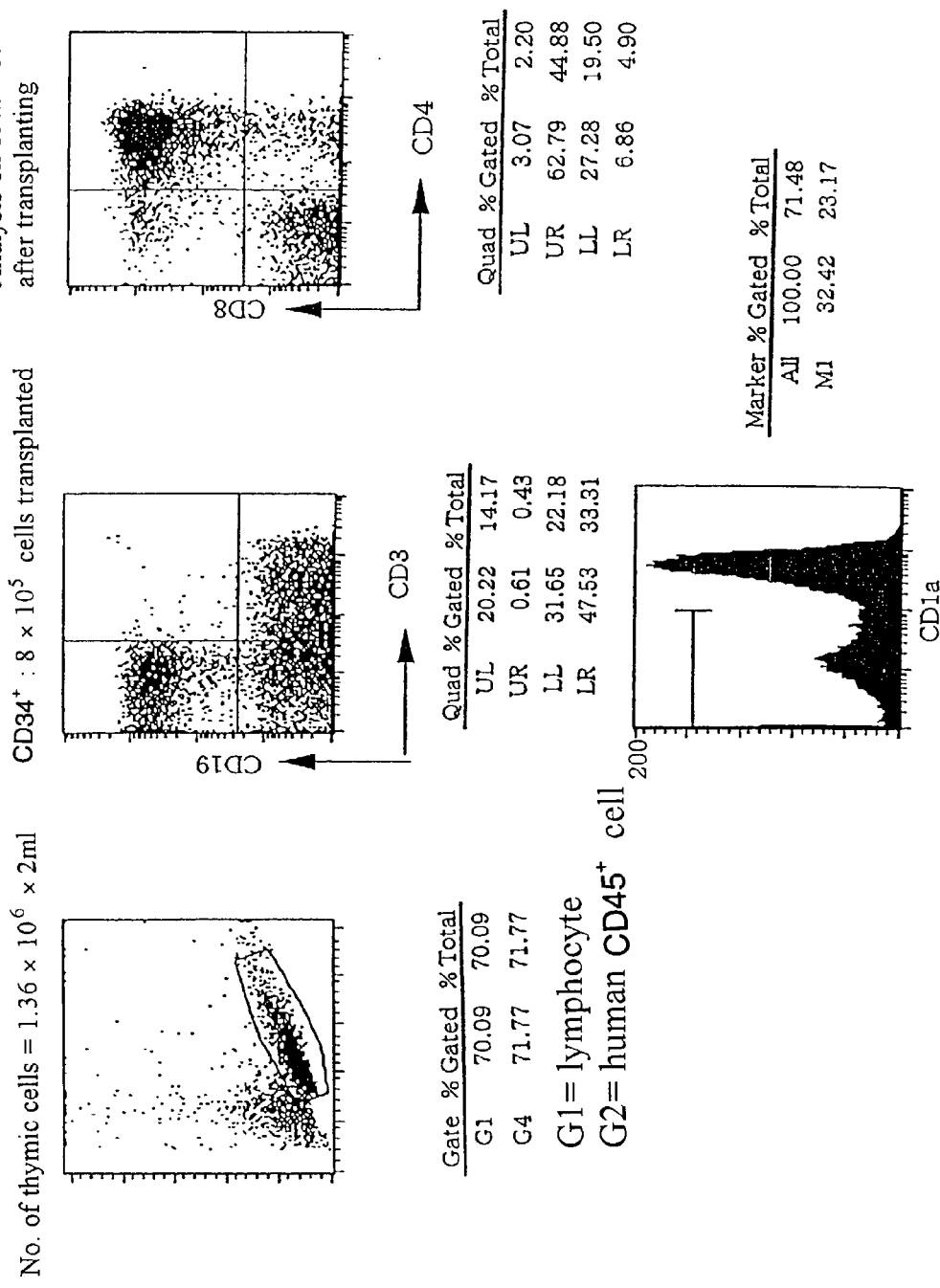
FIGS. 10A and 10B show engraftment and differentiation of human cells in the thymus of the NOG mouse to which human CD34 positive cells have been introduced.
Figure 10B:
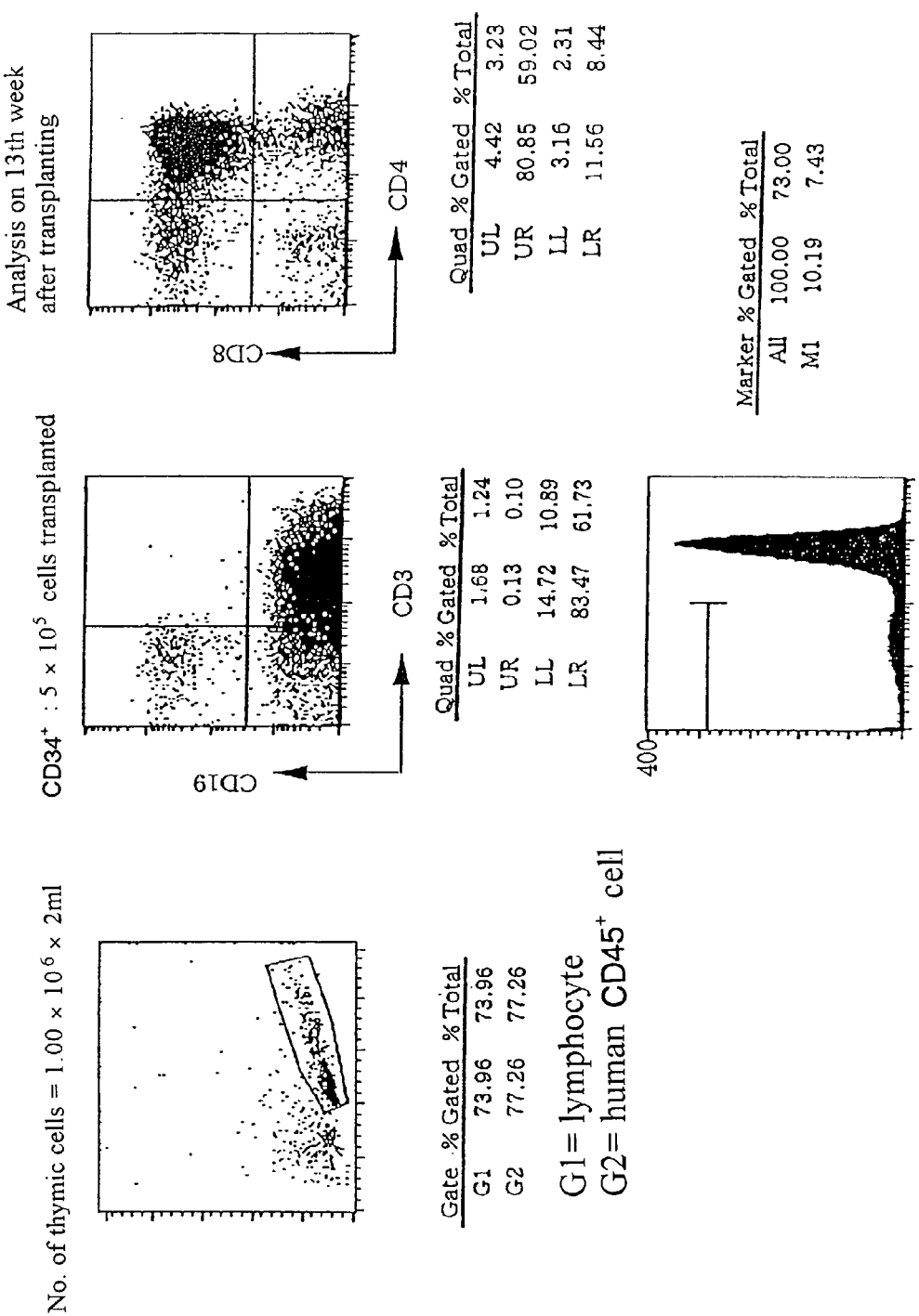
Figure 11A:
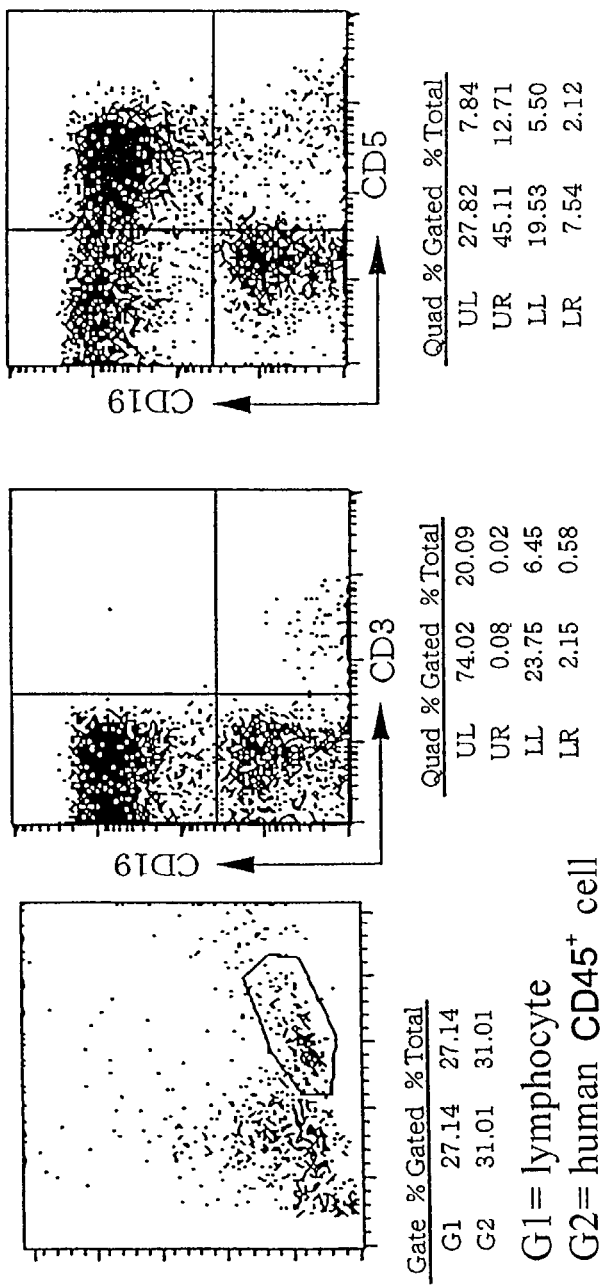
FIGS. 11A and 11B show engraftment and differentiation of human cells in the spleen of the NOG mouse to which human CD34 positive cells have been introduced.
Figure 11B:
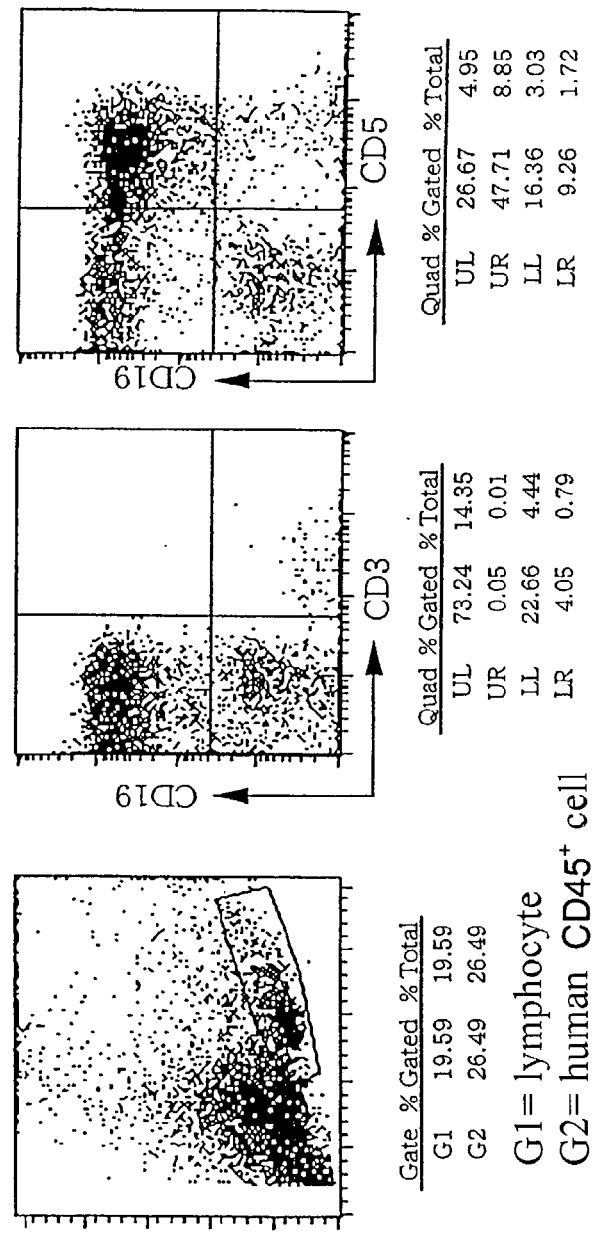
Figure 12A:
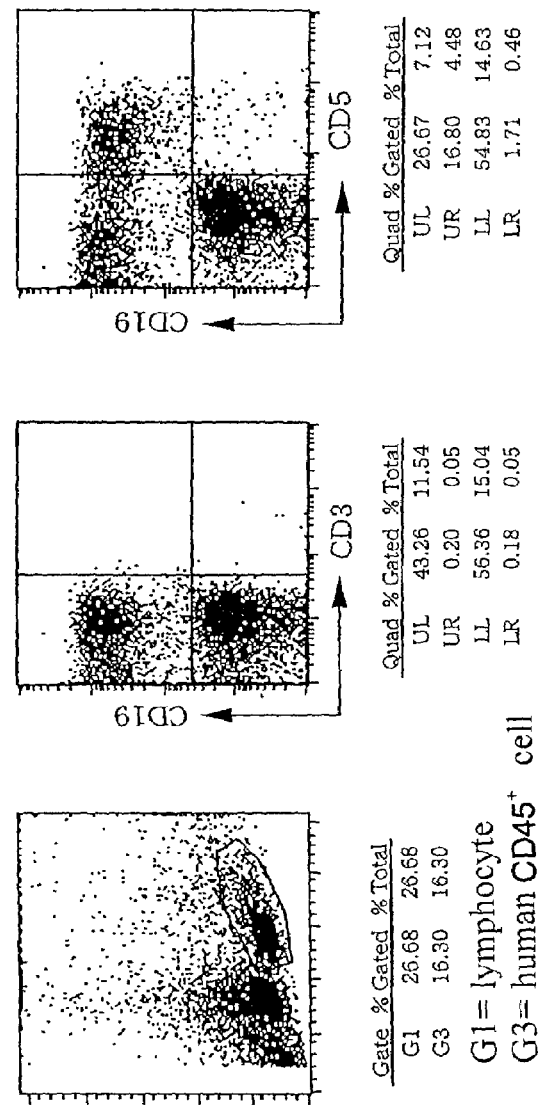
FIGS. 12A and 12B shows show engraftment and differentiation of human cells in the spleen of the NOG mouse to which human CD34 positive cells have been introduced.
Figure 12B:
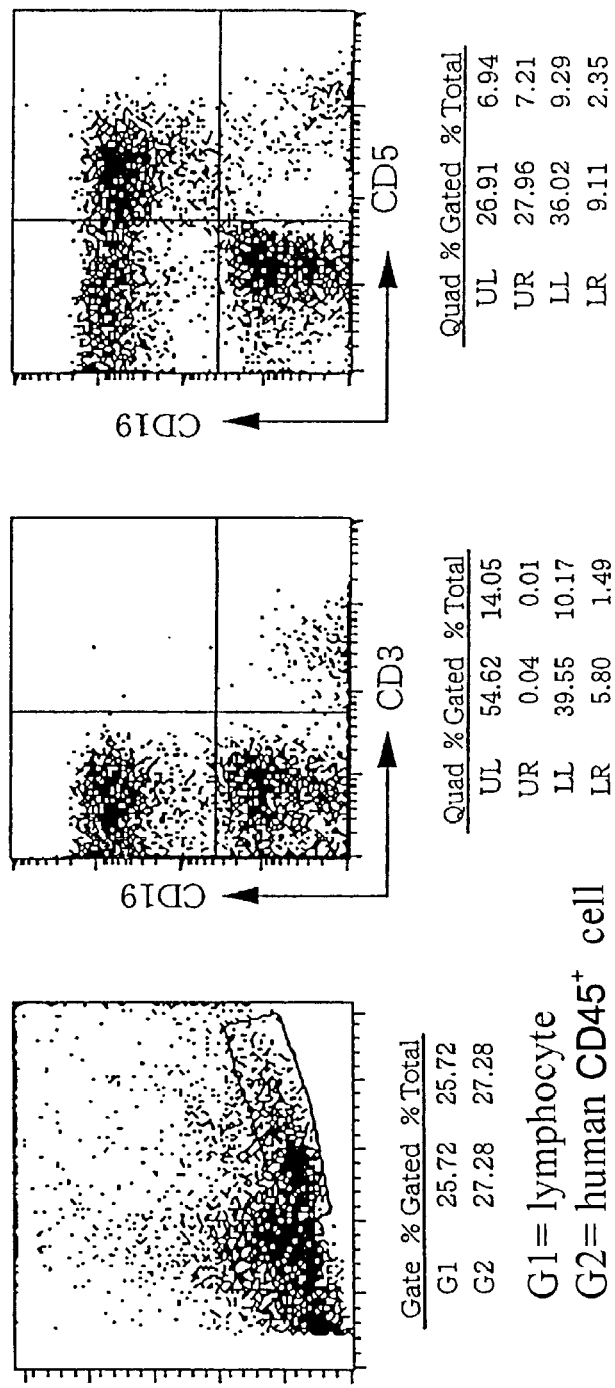

The gene introduction efficiency into CD34 positive cells was 40±5% (n=5). FIG. 8 shows the results of FACS wherein mouse bone marrow cells of primary, secondary, and tertiary transplant mice were stained with human CD45. It was observed that gene-introduced human cells existed in all the mice.

By using NOG mice of the present invention as a host, the inventors became the first in the world to successfully accomplish the introduction of a gene capable of being expressed in hematopoietic stem cells which can be transplanted to up to a tertiary host. Use of conventional NOD-scid mice enabled up to secondary transplant (Guenechea G et al., Nature Immunol, 2, 75–82, 2001), and beyond this it was shown that the present mice were more sensitive and useful as an assay system for hematopoietic stem cells.

EXAMPLE 4

Production of Complete Human Antibodies Using NOG Mice

After NOG mice (8 week-old) and NOD/Shi-scid mice (8 week-old) were irradiated with 2.5 Gy and 3.5 Gy, respectively, they were subjected to intravenous transplant of $1\times10^6$ of CD34$^+$ cells which were purified with magnet beads from human umbilical cord blood (provided by Tokai University, Cell Transplant Research Center, with the consent and approval of the pregnant women). Specifically, MNC was isolated from umbilical cord blood using Ficoll, and then CD34$^+$ cells were isolated by MACS immunomagnetic separation system (Miltenyl Biotec, Glodach, Germany). After confirming that the CD34$^+$ cells had 97% or more purity by FACS, they were used for transplant.

Blood, having been chronologically taken from orbits, and after MNC fraction was obtained by Ficoll, was stained with fluorescence-labeled CD45, CD19, and CD3 antibodies (Becton Dickinson, San Jose, Calif.). The reconstruction of human lymphocytes, and the ratios of B-cells and T-cells were confirmed with CD45, and fluorescence-labeled CD19 and CD3, respectively, by FACS.

Moreover, thymuses and spleens were extracted from these mice, cells were prepared therefrom, the cell numbers were counted, and they were stained with various fluorescence antibodies (Becton Dickinson, San Jose, Calif.). Then, they were analyzed by FACS in the same manner as the above reconstruction confirmation.

From 6 or 8 weeks after the transplant, antigens had been administered to these mice. As an antigen, DNP-KLH was used. The immunization was performed intraperitoneally with 100 μg/mouse of DNP-KLH together with an adjuvant of aluminum hydroxide (ALUM). The same immunization was performed every two weeks and serum was taken for measuring antibody titer by ELISA.

At this juncture, ELISA was performed as follows.

96-well plate was coated with anti human IGs (ICN, Aurora, Ohio) or DNP-KLH, and blocking and washing were performed with 3% BSA. Diluted anti serum was added thereto. After the reaction at room temperature for 2 hours, washing was performed. Then, biotinylated anti human IgM or anti human IgG monoclonal antibodies (Phermingen, San Diego, Calif.) were added. After the reaction at 37° C. for 2 hours, washing was performed. Then, avidinylated peroxidase was added for 1 hour reaction at room temperature. The plate was washed and TMB peroxidase EIA substrate kit solution (Bio-Rad Laboratories, USA) was added for 30-miniute reaction at room temperature. Then, the reaction was inhibited with 10% HCl, and the absorbance was measured at 450 nm. The Ig concentration was calculated in accordance with the standard curve.

(1) Efficiency of Transplanting and Reconstituting CD34$^+$ Cells Derived From Umbilical Cord Blood With respect to the ratio of human CD45$^+$ cells in the NOG mice after transplanting the umbilical cord blood cells, the ratio of human CD45 in peripheral blood was gradually decreased from 4 weeks onward. However, from 12 weeks onward, suddenly the ratio of increase of T-cells became high, and along with this, it was observed that the ratio of human CD45 was also increased in some mice (Table 3). Increases of the CD45$^+$ ratio, caused by such T-cell increase, had never been observed in peripheral blood of the existing NOD/Shi-scid mouse. These NOG mice had never been affected with GVHD until 14th week.

TABLE 3

| SCT Gp. | Source | SCT | CD34+ cells | 4 weeks % CD45 | 4 weeks % CD19 | 4 weeks % CD3 | 6 weeks % CD45 | 6 weeks % CD19 | 6 weeks % CD3 | 8 weeks % CD45 | 8 weeks % CD19 | 8 weeks % CD3 | 10 weeks % CD45 | 10 weeks % CD19 | 10 weeks % CD3 | 12 weeks % CD45 | 12 weeks % CD19 | 12 weeks % CD3 | remarks |
|---|---|---|---|---|---|---|---|---|---|---|---|---|---|---|---|---|---|---|---|
| 2nd SCT | CB2 | freeze thawing | $1.0 \times 10^6$ | 47.3 | 45.7 | 13 | N.A. | N.A. | N.A. | 27.5 | 42.7 | 7.2 | 19.8 | 27.9 | 4.9 | | | | |
| | PBSC1 | freeze thawing | $1.8 \times 10^6$ | 79.5 | 0.7 | 13.4 | 72.5 | 22.9 | 47.7 | 13.3 | 14.3 | 65.7 | | | | | | | Analyzed because of death at 8-week |
| | PBSC2 | freeze thawing | $1.8 \times 10^6$ | 30.8 | 3.0 | 0.1 | 62.0 | 63.2 | 3.8 | 68.5 | 93.6 | 2.1 | 13.7 | 64.5 | 23.9 | 10.3 | 48.4 | 32.6 | |
| | PBSC3 | freeze thawing | $1.8 \times 10^6$ | 26.9 | 3.7 | 0.0 | N.A. | N.A. | N.A. | 43.5 | 62.0 | 7.6 | 28.4 | 34.1 | 11.1 | 22.0 | 35.5 | 14.0 | |
| 3rd SCT | CB | fresh | $1.8 \times 10^5$ | 4.8 | 5.7 | 0.1 | 82.2 | 95.9 | 0.0 | 12.4 | 79.1 | 1.0 | 21.8 | 71.7 | 10.1 | | | | |
| | BM | freeze thawing | $1.9 \times 10^5$ | 1.7 | 0.0 | 0.0 | 8.2 | 48.2 | 0.0 | 13.5 | 49.8 | 0.0 | 7.0 | 73.7 | 0.0 | | | | mixed |
| | PBSC2 | freeze thawing | $1.65 \times 10^6$ | 1.4 | 2.0 | 0.0 | 51.6 | 91.7 | 0.0 | 25.6 | 91.4 | 0.0 | 25.8 | 85.6 | 0.1 | | | | |
| | PBSC3 | freeze thawing | $1.65 \times 10^6$ | 2.1 | 1.3 | 0.2 | 24.1 | 88.4 | 0.0 | 45.3 | 90.2 | 0.0 | 14.3 | 82.5 | 0.0 | | | | |
| 4th SCT | PBSC1 | freeze thawing | $5.0 \times 10^5$ | 19.4 | 2.6 | 0.0 | 27.7 | 39.8 | 0.0 | 39.2 | 92.4 | 0.1 | | | | | | | |
| | PBSC2 | freeze thawing | $5.0 \times 10^5$ | 14.5 | 1.8 | 0.1 | 20.0 | 17.4 | 0.2 | 33.4 | 82.1 | 0.0 | | | | | | | mixed |
| | PBSC3 | freeze thawing | $5.0 \times 10^5$ | 22.1 | 3.3 | 0.0 | 17.5 | 49.1 | 0.1 | 26.1 | 83.4 | 0.1 | | | | | | | |
| 5th SCT | BM | freeze thawing | $1.5 \times 10^5$ | 0.9 | * | * | 0.2 | * | * | | | | | | | | | | |
| 6th SCT | BM1 | fresh | $3.6 \times 10^5$ | | | | | | | | | | | | | | | | |
| | BM2 | fresh | $3.6 \times 10^5$ | | | | | | | | | | | | | | | | |
| | PBSC1 | freeze thawing | $9.0 \times 10^5$ | | | | | | | | | | | | | | | | CD3 eliminated |
| | PBSC2 | freeze thawing | $9.0 \times 10^5$ | | | | | | | | | | | | | | | | CD3 eliminated |
| | PBSC3 | freeze thawing | $9.0 \times 10^5$ | | | | | | | | | | | | | | | | CD3 eliminated |

Reconstitution of human cells in NOG mice: peripheral blood (2) T-Cell Differentiation in NOG Mice A. T-Cell Differentiation in the Thymus FIGS. 9A, 9B, 10A and 10B show T-cell differentiation patterns in thymuses. As shown in the figures, CD3 positive cells were differentiated in the thymuses of these mice, and it was indicated that these cells contained CD4/CD8 DN (Double negative), DP (Double positive), and SP (Single positive) as well as those cells in a normal thymus or detected by hu/m-RTOC, and a part of them were mature to be CD1a-low T-cells in 11th or 13th week after transplanting. The number of the thymic cells was 1 to $2 \times 10^6$ and this was about one-hundredth of the number of thymic cells in a normal mouse. This phenomenon was observed also in NOD/Shi-scid mice, but its frequency was remarkably low, such as 8/28 (28.6%). As opposed to this, NOG mice had a frequency of 7/7 (100%).

B. T-Cells at Peripheries

FIGS. 11A, 11B, 12A, 12B, 13A, and 13B show further analysis on T-cells in splenic cells or peripheral blood. CD3 positive cells were observed even at the peripheries of the mice from which T-cell differentiation was observed in their thymuses. These are a group of CD4/CD8 positive cells, and this indicated that there was the possibility that they included cells differentiated in thymuses.

(3) B-Cell Differentiation in NOG Mice

A. Subset Differentiation of B-Cells

Figure 14A:
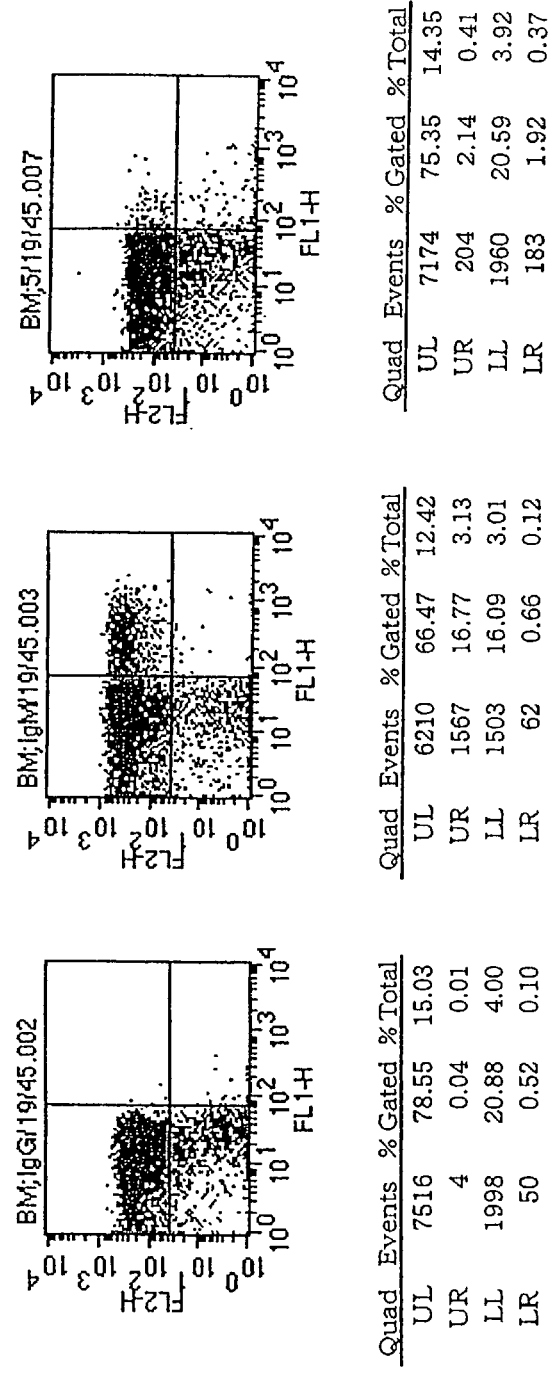
FIGS. 14A and 14B show engraftment and differentiation of human cells in bone marrow of the NOG mouse to which human CD34 positive cells have been introduced.
Figure 14B:
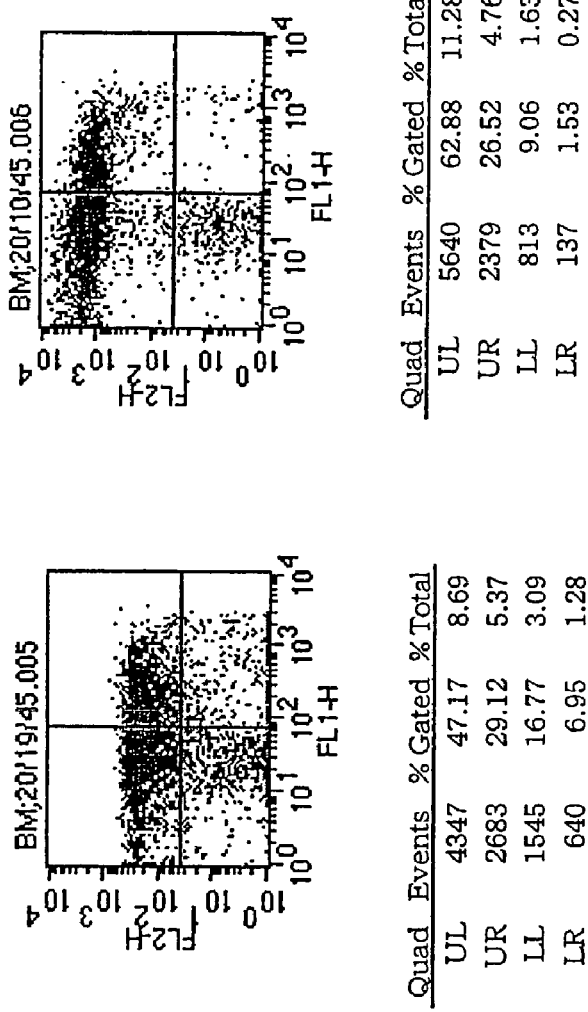

Also, FIGS. 14A and 14B show the expression ratios of CD5 by B-cells among bone marrow cells. In bone marrow, the differentiation of CD5 positive cell, so-called B1a cells, was not facilitated, and groups of CD19 positive or IgM positive cells were dominant. Further, cells in a group in which IgM is highly positive expressed CD20. No abnormality was detected on the differentiation of human B-cells in the bone marrow of these mice. This phenomenon is also observed in B-cell differentiation in NOD/Shi-scid mice, and thus it is considered a common quality.

B. B-Cell at Peripheries

Figure 13A:
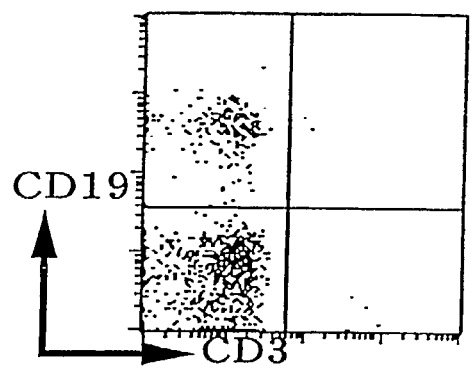
FIGS. 13A and 13B show engraftment and differentiation of human cells in peripheral blood of the NOG mouse to which human CD34 positive cells have been introduced.
Figure 13A:
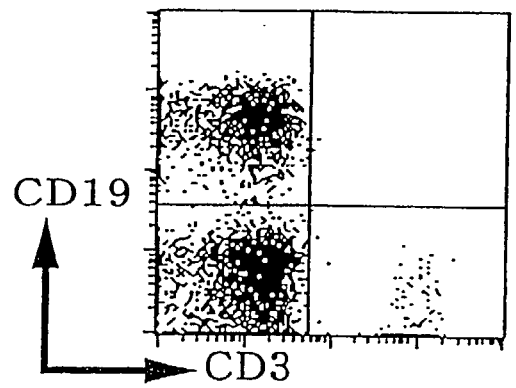
Figure 13B:
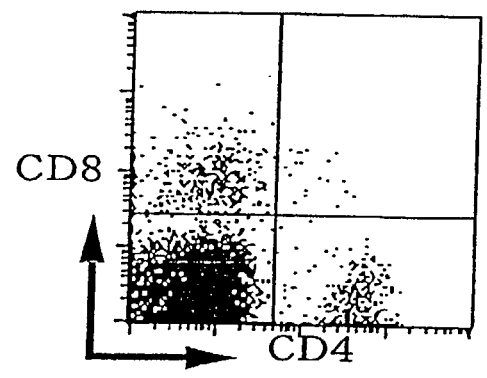
Figure 13B:
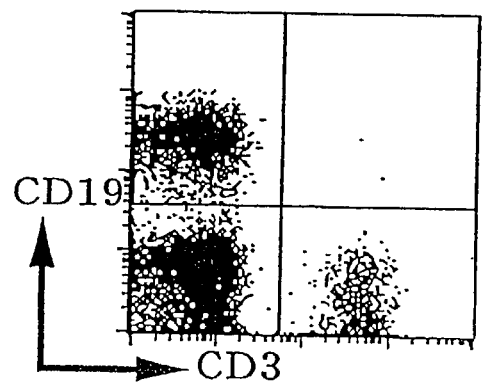

FIGS. 13A and 13B show FACS patterns of B-cells at their peripheries. The ratios of B-cells were almost the same as those in NOD/Shi-scid mice. However, in spleens, CD5 positive cells, so-called B1a cells which was a subgroup of B-cells were dominant, and a large difference was detected from differentiation patterns in bone marrow. On the other hand, IgM positive CD5 negative cell groups were also detected at a ratio of about 20% and thus this proved that cells, other than B1a cells, were also detected.

(4) Antibody Production Ability in NOG Mice

Figure 15A:
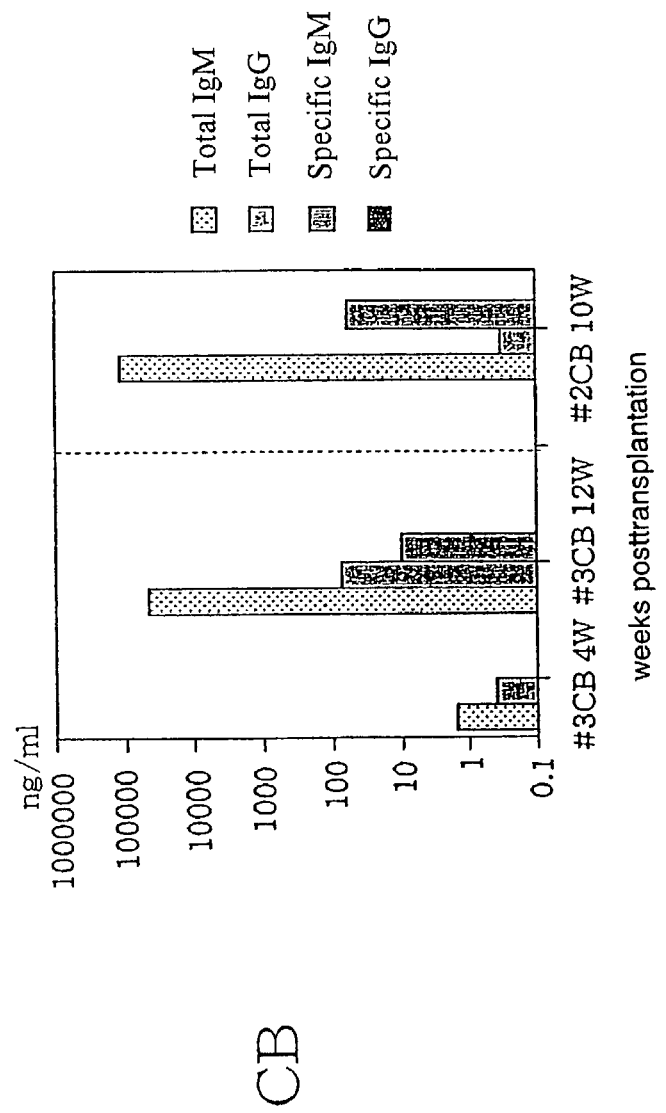
FIGS. 15A, B and C show the ability of NOG mouse transplanted with umbilical cord blood (CB), bone marrow (BM) and peripheral blood stem cells (PBSC), respectively, to produce human antibodies.
Figure 15B:
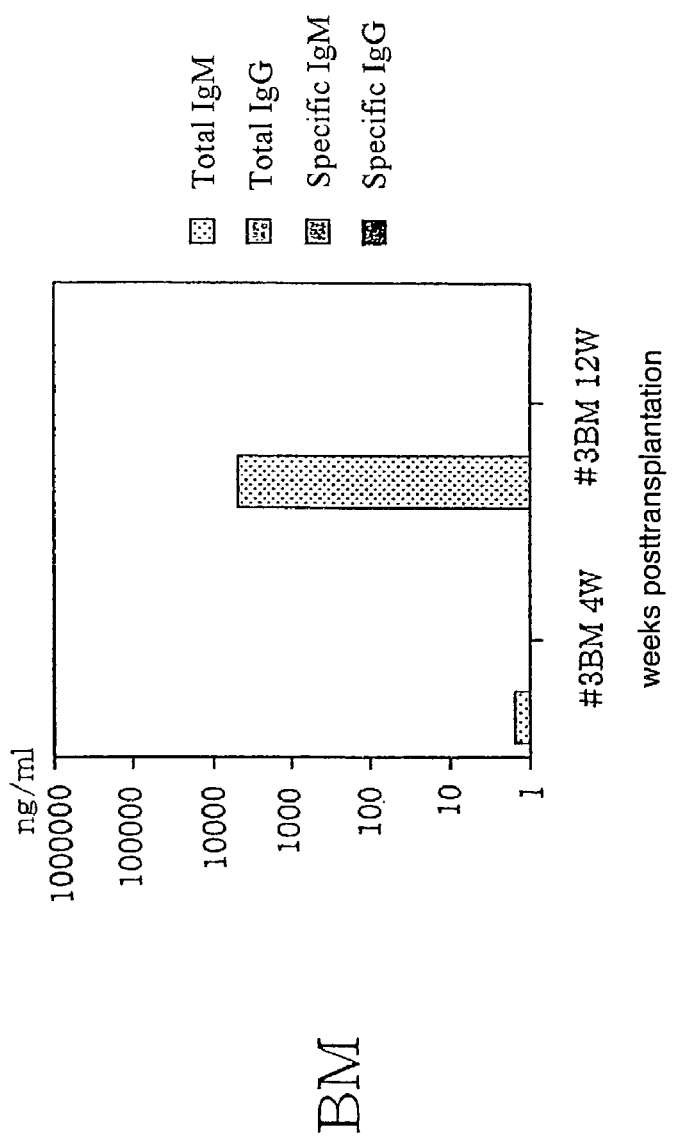
Figure 15C:
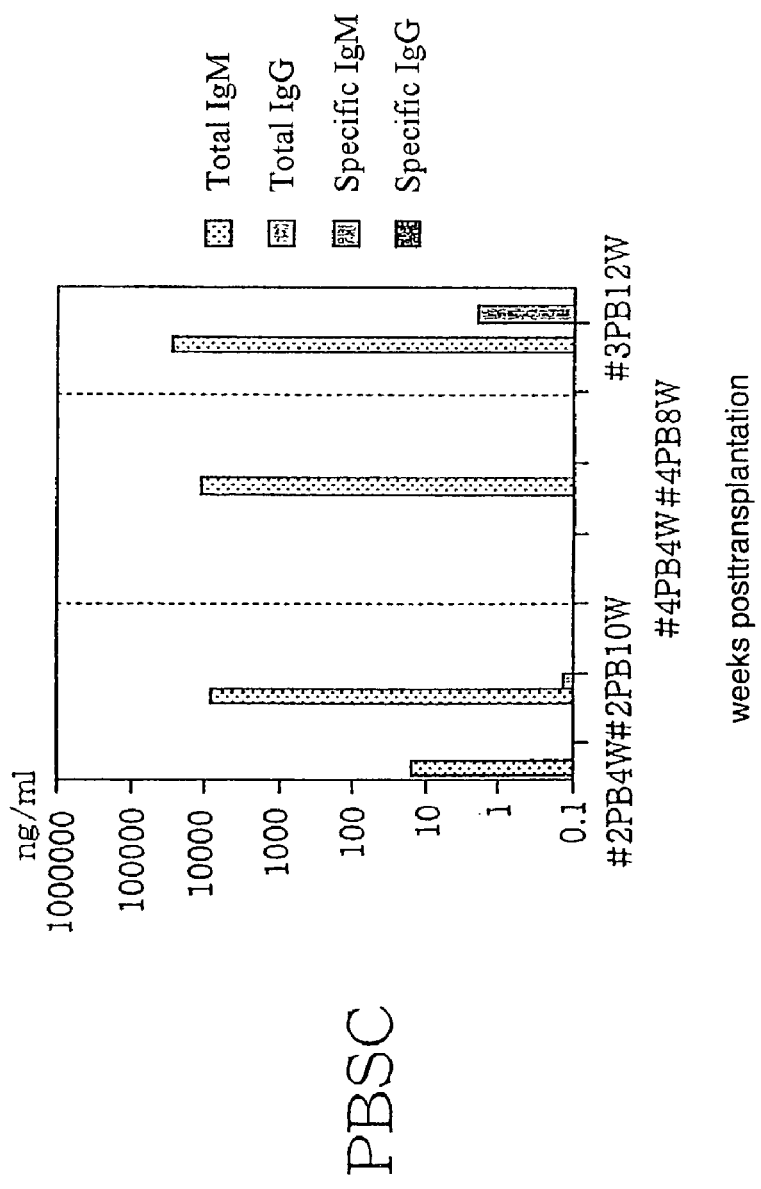

DNP-KLH was administered as an antigen to these mice, and IgM and IgG antibody production amounts were chronologically measured. As a result, antigen non-specific IgM and IgG antigen specific IgM were detected by repeating the administration three times. Although T-cells were detected in thymuses and peripheries, antigen specific IgG production was not detected. (FIGS. 15A, 15B and 15C) FIGS. 15A, 15B and 15C also show the results of mice having transplanted thereto CD34$^+$ cells derived from bone marrow (BM) (FIG. 15B) and peripheral blood (PBSC) (FIG. 15C). In bone marrow and peripheral blood, there was observed a tendency of lower productions of specific IgM and non-specific IgG as compared with the production in umbilical cord blood.

The above results indicate that the present mouse differentiates human T-cells and B-cells and is valuable for use in human antibody production systems.

EXAMPLE 5

Neoplasm Proliferation System

NOD/Shi-scid mice, NOG mice, BALB/cAJcl-nu mice (purchased from CLEA), and C.B-17/Icr-scid mice (purchased from CLEA) were used. All the used mice were 5 weeks old or older.

As cells to be transplanted to the mice, transplant human tumor cell line, LM-2-JCK was used. LM-2-JCK was a cell line which was established from lymphoblast lymphoma of a 13-year-old female patient and maintained by successive heterografts to nude mice. It has been reported that though LM-2JCK expresses T-cell antigen CD4 and CD5, it does not express other cell antigens including antibodies.

A solid tumor which was subcutaneously passaged 12 times in nude mice was used for heterograft assay. The tumor was chopped into pieces in F-10 nutrition supplementary medium (GIBCO BRL) by scissors and fully dispersed by a pipette, and then cell suspension was prepared by passing through a nylon mesh. The concentration of viable cells in the suspension was calculated by trypan blue stain (GIBCO BRL). After centrifugation, tumor cells were dispersed at concentrations of $1 \times 10^7$ and $1 \times 10^6$ viable cells/ml into physiological saline. The tumor cell dispersion liquid was subcutaneously injected, in an amount of 0.1 mL, at both flanks of mice by using 1 ml syringe equipped with 25 gage needle. After the injection of the tumor cells, the size of the tumor and the body weight were measured at intervals of one week. On the 21st day after the $1 \times 10^6$ cells were transplanted, when the tumor became large, the mice were sacrificed and the weights and sizes of the tumors were measured.

The difference in transplantability of LM-2-JCK among the mice having different backgrounds is shown in Table 4.

TABLE 4

Heterotransplantation of LM-2JCK to mice having different genetic backgrounds

| Mouse strain | No. of cells grafted | Observation period | No. of tumor-engrafted mice/No. of transplanted mice | Weight of tumor a) |
|---|---|---|---|---|
| NOG | $10^6$ | 21 days | 10/10 (100%) | 3.97 ± 2.10 b) |
| NOD/Shi-scid | $10^6$ | 21 days | 10/10 (100%) | 1.34 ± 0.77 |
| C.B-17/Icr-scid | $10^6$ | 21 days | 8/10 (80%) | 1.21 ± 1.06 |
| NOG | $10^5$ | <9 weeks | 8/8 (100%) c) | n.t. |

TABLE 4-continued

Heterotransplantation of LM-2JCK to mice having different genetic backgrounds

| Mouse strain | No. of cells grafted | Observation period | No. of tumor-engrafted mice/No. of transplanted mice | Weight of tumor a) |
|---|---|---|---|---|
| NOD/Shi-scid | $10^5$ | <9 weeks | 5/10 (50%) | n.t. |
| C.B-17/Icr-scid | $10^5$ | <9 weeks | 0/10 (0%) | n.t. | a) The weight of tumor was measured 21 days after the transplanting and indicated with average ± SD(g).
b) As to NOD/Shi-scid and C.B-17/Icr-scid, when p < 0.05 (t-test), the significant difference is observed.
c) As to NOD/Shi-scid (p < 0.05) and C.B-17/Icr-scid (p < 0.01), the significant difference is observed. ($\chi^2$ test)
n.t.: not tested In the case of the transplant of $1 \times 10^6$ cells, all the tumors were engrafted in NOG mice and NOD/Shi-scid mice. In contrast, the engraftment ratio for C.B-17/Icr-scid was 80%.

The tumor engraftment ratios in these strains were lower in the case of the transplant of $1 \times 10^5$ cells, and particularly tumor proliferation was not observed in any of the C.B-17/Icr-scid mice.

Figure 16:
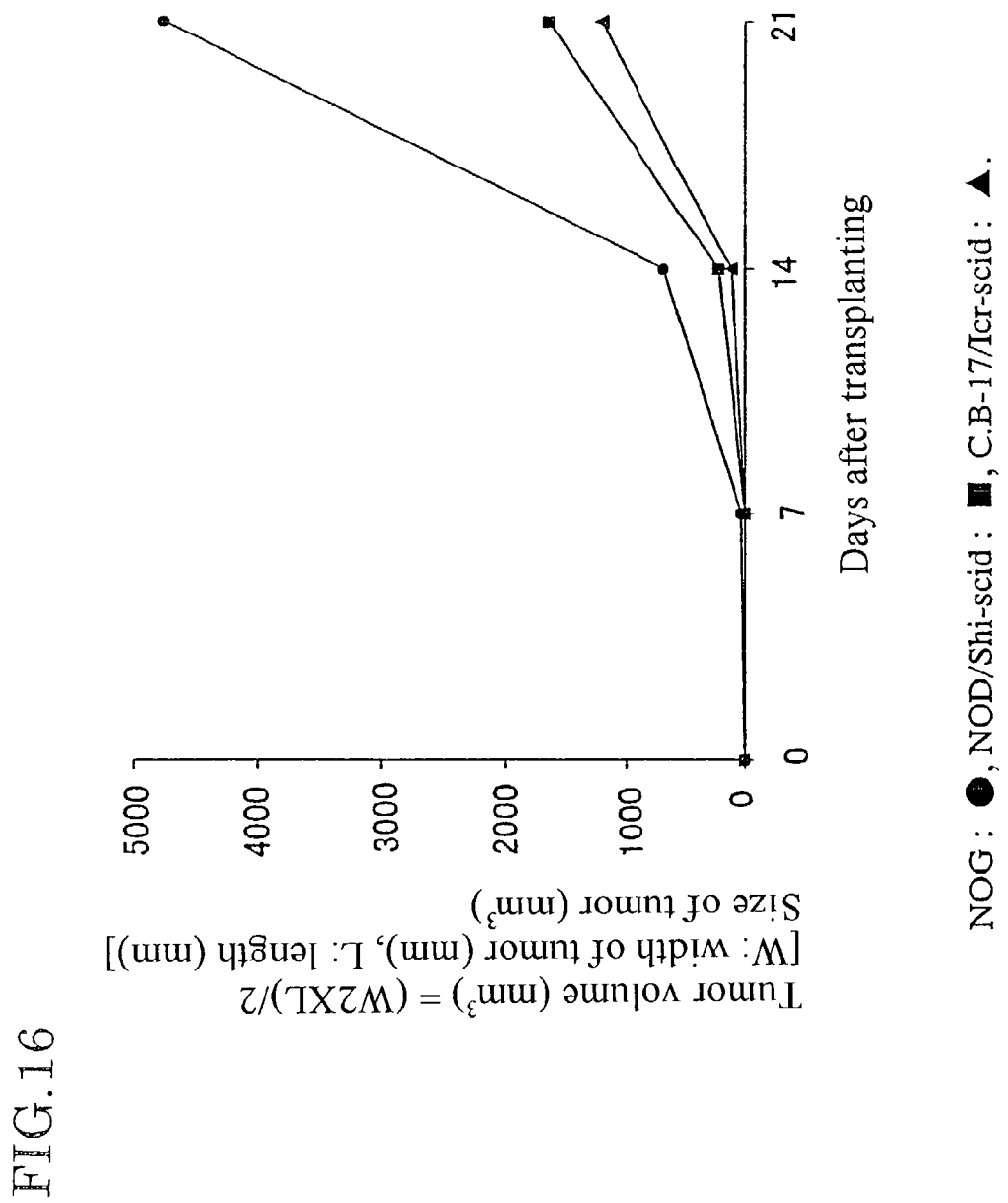
FIG. 16 shows the tumor formations after transplanting LM-2-JCK to each mouse strain.

In the case of the transplant of $1 \times 10^6$ cells, the growth curves of the tumors are shown in FIG. 16.

The tumor proliferation in NOG mice exceeded that of the other 2 strains.

On the 21st day, the NOG mice had 2.89 and 3.97 times larger average tumor volume than the NOD/Shi-scid mice and C.B-17/Icr-scid mice, respectively, had on the same day, and significant differences were observed by Student t-test. (p<0.001)

No significant difference was observed in the average volume on the 21st day between tumors engrafted in NOD/Shi-scid mice and tumors engrafted in C.B-17/Icr-scid mice.

EXAMPLE 6

Establishment of HIV-Infection Model System Using NOG Mice

Establishment of HIV-infection model system using NOG mice was examined by use of various HIV lines. Typical examples are shown below.

NOG mice were used in this example. For comparison, NOD/Shi-scid mice were also used, which were produced before by backcrossing both mutants of C.B-17-scid mice and NOD/Shi mice with each other.

HIV-1 used herein was a JRFL virus which was isolated from frontal lobe tissue of a patient with AIDS-associated encephalopathy and had infectivity on a DNA-cloned macrophage and T-cells. Further, a GFP-HIV-1 in which a JRFL virus and a GFP gene were incorporated at env V3 region and downstream of gp41, respectively was used.

(1) Production of Mice (hu-PBL-NOG Mice) to Which Human Mononuclear Lymphocytes are Transplanted $1 \times 10^7$ per mouse of peripheral blood human lymphocytes (PBL), provided by a normal person with consent and approval for test use, were intraperitoneally inoculated directly into NOG mice. For comparison, the PBL from the same donor was intraperitoneally inoculated into NOD/Shi-scid mice having a normal IL-2Rγ chain.

(2) Infection of Mice With HIV-1

On the 6th day after the PBL inoculation, 1,000 TCID$_{50}$ of viruses were intraperitoneally inoculated into mice. The mice were sacrificed 2 weeks after the virus infection and ascites including abdominal exudates cells were collected. The number of human cells in the ascites was calculated by FACS. Further, spleens were extracted and fixed by paraformaldehyde, and then made into paraffin-embedded sections.

(3) Pathological Analysis

The spleen tissue sections were subjected to HE-stain, and further to immunostaining using antibodies against human CD3, CD4, CD8, and HIV-1p24 antigens. For immunohistologic stain, in addition to conventionally reported ABC method, EPOS method and Envisiont method were employed.

The engraftment of human cells in hu-PBL-NOG mice was evaluated.

A series of examination results are shown in Table 5.

TABLE 5

HIV-1 infection test on human PBMC grafted-NOG mice female without TM β1 non existant PBL NOG mice PBL transplantation total PBL 160 mL 4.37 × $10^8$ cells
2 × $10^7$ cells per mouse
Donor A
14 NOG mice (6 males, 8 females)

| Infection NOG mice | | |
|---|---|---|
| JRFL | M-tropic | 3 males |
| NL4-3 | T-tropic | 3 males |
| JRCSF | M-tropic | 3 females |
| NLCSFV3EGFP | M-tropic | 2 females |
| MOCK | | 3 females |

| | 13th day after infection | | | |
|---|---|---|---|---|
| | Cell number ×$10^4$ cells | % HLA | % CD4 | % CD8 | p24 |
| 1. Mock | | | | | |
| Ascites | 75 | 67.7 | 21.4 | 56.4 | |
| Spleen | 510 | 71.8 | 13.8 | 45.5 | |
| PBL | 430 | 77.9 | 16.8 | 49.9 | 0 |
| 2. Mock | | | | | |
| Ascites | 130 | 67.6 | 14.8 | 60.5 | |
| Spleen | 698 | 63.3 | 12.7 | 49.2 | |
| PBL | 86 | 66.6 | 11.6 | 55.5 | 0 |
| 3. Mock | | | | | |
| Ascites | 110 | 62.3 | 36.4 | 44.2 | |
| Spleen | 434 | 61.3 | 20.9 | 45.2 | |
| PBL | 93 | 34.7 | 20.6 | 44.7 | 0 |

TABLE 5-continued

4. JRFL

| | | | | | |
|---|---|---|---|---|---|
| Ascites | 152 | 75.5 | 1.7 | 53.9 | |
| Spleen | 335 | 54.6 | 2.8 | 64.6 | |
| PBL | 210 | 42.8 | 2.1 | 77.3 | 3,090 |

5. JRFL

| | | | | | |
|---|---|---|---|---|---|
| Ascites | 220 | 75.8 | 1.8 | 57 | |
| Spleen | 12 | 75.8 | 1.65 | 79.6 | |
| PBL | 870 | 81.1 | 1.8 | 77.9 | 5,445 |

6. JRFL

| | | | | | |
|---|---|---|---|---|---|
| Ascites | 178 | 36.3 | 1.79 | 54.1 | |
| Spleen | 418 | 65.3 | 1.1 | 74.4 | |
| PBL | 65 | 33.1 | 1.72 | 75.6 | 1,961 |

HIV-1 infection to human PBMC grafted-NOG mice (2)

| | Cell number $\times 10^4$ cells | % HLA | % CD4 | % CD8 | p24 |
|---|---|---|---|---|---|
| 7. NL4-3 | small spleen | | | | |
| Ascites | 120 | 7.6 | 9.74 | 74.1 | |
| Spleen | 14 | no FACS | | | |
| PBL | non-existent | | | | |
| 8. NL4-3 | | | | | |
| Ascites | 84 | 73.5 | 1.43 | 45.7 | |
| Spleen | 465 | 53 | 1.64 | 60.0 | |
| PBL | 26 | 11.3 | 4.59 | 49.3 | 118 |
| 9. NL4-3 | | | | | |
| Ascites | 110 | 8.1 | 9.33 | 80.6 | |
| Spleen | 17 | 14.8 | 19.1 | 23.5 | |
| PBL | 3 | 0.6 | 13.0 | 27.8 | 0 |
| for three male NL4-3, their ears were excised. | | | | | |
| 10. JRCSF | | | | | |
| Ascites | 320 | 29.9 | 0.77 | 93.7 | |
| Spleen | 230 | 67 | 1.85 | 74.9 | |
| PBL | 49 | 33.7 | 0.48 | 71.7 | 3,132 |
| 11. JRCSF | | | | | |
| Ascites | 63 | 68.5 | 3.18 | 41.6 | |
| Spleen | 390 | 68.7 | 3.58 | 85.8 | |
| PBL | 121 | 2.9 | 4.5 | 31.5 | 4,180 |
| 12. JRCSF | poor construction | | | | |
| Ascites | 110 | 15.2 | 23.0 | 62.4 | |
| Spleen | 380 | 14.5 | 2.98 | 89.8 | |
| PBL | 110 | 44.7 | 2.06 | 89.4 | 864 |
| 13. NLCSFV3EFFP | GFP+ of spleen and PBL are 0.1% or less | | | | |
| Ascites | 43 | 72.5 | 2.26 | 69.8 | |
| Spleen | 250 | 50.8 | 0.77 | 67.7 | |
| PBL | 124 | 76.5 | 5.07 | 63.3 | 271 |
| 14. NLCSFV3EGFP | GFP+ of ascites, spleen and PBL are 0.2 to 0.3% or less | | | | |
| Ascites | 110 | 44.3 | 6.36 | 76.3 | |
| Spleen | 560 | 2.7 | 23.3 | 44.4 | |
| PBL | 127 | 3.4 | 5.26 | 84.2 | 114 |

CD4 positive cells were specifically killed by all the HIV viruses.

Conventionally, it has been reported that only M-tropic viruses can proliferate in mice and CD4 positive cells are killed, but T-tropic viruses can proliferate in NOG mice.

It was found that human CD4 positive T-cells and CD8 positive T-cells were each engrafted around central arteries of spleens of the mice to which human peripheral blood was transplanted. With respect to the number of human CD3 positive cells, NOG mice had obviously a larger number of human cells than NOD/Shi-scid mice. According to the measurement by FACS, there were $1\times10^7$ or more human CD4 positive cells on average in ascites.

On the other hand, CD4 positive cells were hardly detected from NOD/Shi-scid mice and almost all the detected cells were CD8 positive cells. In the example previously described, the antibodies (TMβ-1) (0.5 mg per mouse) which were against mouse IL-2 receptor β chain and suppressed the differentiation of NK cells were intraperitoneally injected into the NOD/Shi-scid mice 3 days before the inoculation of human PBL. However, this treatment was not conducted in this example. It has been already confirmed in other tests that antibody-treated mice would have many CD4 and CD8 positive human cells engrafted to them. Still though the number of human cells from NOG mice was apparently 3 to 4 times more than the number of cells from NOD/Shi-scid mice that had been subjected to the antibody treatment.

In the HIV-infected mice, p24 positive cells which were HIV antigens were detected around spleen arteries. Further, in spleens and ascites of the HIV-infected mice which express GFP, cells with GFP expression were clearly detected. The number of virus-infected cells of NOG mice was apparently larger than that of NOD/Shi-scid mice.

EXAMPLE 7

Establishment of HTLV-1 Infection Model System Using NOG Mice $2\times10^7$ cells per mouse of MT-2 cells which were cell lines derived from HTLV-1 leukemia, were transplanted to NOG mice.

In the 4th week after the transplant, the mice having lymphomas formed therein (Table 6) were counted, and it was checked whether or not the mice having lymphomas were infected with a HTLV gene, by Southern blotting and PCR. As a result of a pathological search, dermal lymphoma and posterior intraperitoneally bilateral lymphomas are observed. The mice having a large tumor had metastasis in lymph nodes around the stomach and had cancer cells infiltrated in a pleura thereof. Further, HTLV positive cells increased in peripheral blood. This indicated a typical onset of leukemia. Moreover, lung-interstitial invasion was also observed. All of these cells expressed Tax protein, but there was no intracerebral invasion.

TABLE 6

1. Transplantation of HTLV-infected cells to NOG mice $2\times10^7$ cells per mouse

| | No. of mice | TMβ-1 | Cell treatment by gamma ray | No. of mice having lymphoma (after 1 month) |
|---|---|---|---|---|
| NOD/Shi-scid mice | 5 | — | — | 0 |
| NOG mice | 40 | — | — | 33(82.5%) |
| NOG mice | 4 | — | 20,000 rad | 0 |
| NOG mice (no cell transplanted) | 2 | — | — | 0 |

EXAMPLE 8

Examination of Leukemic Changes by Introducing Neoplastic Cells and Transplantability of HTLV-1 Positive Cells Using NOG Mice Transplant tests of various HTLV-1 cell lines and tumor formation tests were performed on NOG mice and the usefulness of the mice was examined.

Using 3 samples of HTLV-1 leukemia derived cell lines [L=Leukemic cell lines: ED-40515(−), MT-1 and TL-Oml], 6 samples of HTLV-1 infected cell lines [IT=infected transformed cell lines: SLB-1, M8116, HUT-102, MT-2, MT-4 and TY9-31MT], $10^{7-8}$ cells/0.5mL were transplanted to NOG mice and NOD/Shi-scid mice subcutaneously at a left posterior auricle thereof, and to some of them subcutaneously at a gluteal region thereof. Then, the tumor size in the mice, tissue image, and the mice with, and those without, leukemia were chronologically compared for examination, and the relations between these and transcription factors such as NFκB or fluctuation of Tax protein were also analyzed.

Within 2 weeks, a tumor with a size of 24×17×11 mm was formed in all cases of HTLV-1 leukemia derived cell lines [L] and exceptionally in SLB-1 of HTLV-1 infected cell line [IT]. In contrast, in 5 out of 6 cases of IT, a tumor with a size of at most 10×10×7 mm was formed, and in the case of M8116 or TY9-31MT, there was almost no tumor formation. (Table 7)

TABLE 7

Development of HTLV-1 infected-cells and leukemia cells in NOG mice and their features in vitro and in vivo

| | | | In vitro | | | | In vivo | | |
|---|---|---|---|---|---|---|---|---|---|
| Cell line | Cell type | No. of mice | proliferation pattern | Il-2 dependence | Tax expression | Cells inoculated (×10$^7$) | Route and site of inoculation | period (days) | size of tumor (mm) |
| ED-40516(−) | L | 1 | separately | − | − | 7.5 | I.m Buttock | 16 | 23 × 18 × 12 |
| | | 7 | separately | − | − | 7.5 | s.c post-auricular | 15–16 | 25 × 18 × 12 |
| | | 3 | separately | − | − | 4 | s.c post-auricular | 16 | 25 × 18 × 12 |
| | | 3 | separately | − | − | 1 | s.c post-auricular | 15 | 22 × 17 × 10 |
| SLB-1 | IT | 1 | clustered | − | + | 7.5 | I.m Buttock | 15 | 20 × 10 × 18 |
| | | 7 | clustered | − | + | 7.5 | s.c post-aricular | 15–16 | 20 × 10 × 18 |
| | | 3 | clustered | − | + | 5 | s.c post-auricular | 15 | 21 × 12 × 17 |
| MT-1 | L | 1 | separately | − | − | 7.5 | I.m Buttock | 20 | 25 × 15 × 10 |
| | | 1 | separately | − | − | 7.5 | s.c post-auricular | 20 | 25 × 15 × 10 |
| | | 3 | separately | − | − | 4 | s.c post-auricular | 24 | 23 × 16 × 12 |
| TI-oml | L | 1 | separately | − | − | 7.5 | I.m Buttock | 20 | 25 × 15 × 10 |
| | | 1 | separately | − | − | 7.5 | s.c post-auricular | 20 | 25 × 15 × 10 |
| | | 3 | separately | − | − | 4 | s.c post-auricular | 20 | 22 × 23 × 8 |
| M8116 | IT | 1 | clustered | − | + | 7.5 | I.m Buttock | 18 | sesame |
| | | 2 | clustered | − | + | 7.5 | s.c post-auricular | 18 | sesame |
| HUT-102 | IT | 1 | clustered | − | + | 7.5 | I.m Buttock | 18 | 10 × 10 × 7 |
| | | 2 | clustered | − | + | 7.5 | s.c post-auricular | 18 | 10 '3 10 × 7 |
| MT-2 | IT | 1 | clustered | − | + | 7.5 | I.m Buttock | 18 | 10 × 10 × 7 |
| | | 2 | clustered | − | + | 7.5 | s.c post-auricular | 18 | 10 × 10 × 7 |
| MT-4 | IT | 1 | clustered | − | + | 7.5 | I.m Buttock | 18 | 5 × 5 × 3 |
| | | 2 | clustered | − | + | 7.5 | s.c post-auricular | 18 | 5 × 5 × 3 |
| TY9-31MT-2 | IT | 1 | clustered | − | + | 7.5 | I.m Buttock | 18 | sesame |
| | | 2 | clustered | − | + | 7.5 | s.c post-auricular | 18 | sesame |

L: leukemia cell line
IT: infected-transformant cell line

The case of this tumorigenic cell line showed that the degree of the emergence of leukemic cells in peripheral blood and the invasion of organs were relatively high, but some cases of nontumorigenic cell lines had higher degrees thereof (e.g. HUT-102, MT-2 etc.). Thus, there were not necessarily correlations between tumorigenicity and the degrees of the emergence of leukemic cells in peripheral blood and the invasion on organs. (Table 8)

TABLE 8

Infiltration of leukemia cells into various organs of NOG mice

| Cell strain | Tumor | peripheral blood (PB) | bone marrow (BM) | liver | spleen | lung | brain | kidney | heart |
|---|---|---|---|---|---|---|---|---|---|
| Ed-40515(−) | +++ | ++ | − | + | + | +− | Spongy +− | ++ | − |
| SLB-1 | +++ | +++ | + | ++ | + | Granular +++ | Spongy ++ | + | + |
| MT-1 | +++ | ++ | − | + | + | + | Spongy +− | − | − |
| TI-oml | +++ | ++ | − | Gaint +++ | + | +− | − | − | − |
| M8116 | + | + | − | − | − | − | − | − | − |
| Hut-102 | ++ | ++ | +++ | Nodule +++ | +++ | Pneumonia + | Spongy +− | − | − |
| MT-2 | ++ | ++ | +− | +− | ++ | +− | − | + | − |
| MT-4 | ++ | + | +− | − | ++ | − | − | − | − |
| TY9-31MT-2 | +− | − | − | − | − | − | − | − | − |

$10^7$ cells of tumorigenic ED-40515(−) were transplanted subcutaneously at a left posterior auricle of NOG mice and NOD/Shi-scid mice and they were compared in tumorigenicity in the second week. A tumor with a size of 22×17×10 mm was formed in the NOG mice, and in contrast a tumor was hardly formed at all in NOD/Shi-scid mice. This revealed that NOG mice were prone to tumor formation. (Table 9)

TABLE 9

Comparison of tumor formation between NOG mice and NOD/Shi-scid mice to which ED-40515(−) cell type was transplanted

| Mouse strain | No. of mice | Cells inoculated ($\times 10^7$) | Survival period (days) | Tumor |
|---|---|---|---|---|
| NOG mouse | 3 | 1 | 15 | +++ |
| NOD/Shi-scid mouse | 3 | 1 | 15 | − |

+++ tumor large enough to visually observe
− tumor which cannot visually be observed For the purpose of investigating whether or not the NOG mice are prone to tumor formation in B-cell type, as well as in T-cell type, $7\times 10^7$ of BJAB cells of which only EBER (EBV-Encoded Small RNA) and a vector were transformed, were transplanted subcutaneously at a left posterior auricle of NOG mice. In the 3rd week, they were compared in tumorigenicity. A significantly large tumor (26×18×7/13×18×3 mm) was formed in the mice with BJAB-EBER compared to the mice with BJAB-VECTOR. The tumor size thereof was comparable to that in the case of ED-40515(−) in the above example. (Table 10)

TABLE 10

Proliferation of BJAB-EBER cell line BJAB-VECTOR cell line in NOG mice

| Cell line | Gene introduction | No. of mice | Cells inoculated ($\times 10^7$) | Route and site of inoculation | Survival period (days) | Tumor size (mm) | Weight of tumor |
|---|---|---|---|---|---|---|---|
| BJAB-EBER | gene introduced | 3 | 7 | s.c. post-auricilar | 21 | 26 × 18 × 7 | 2.86 g |
| BJAB-VECTOR | gene not introduced | 3 | 7 | s.c. post-auricular | 21 | 13 × 18 × 3 | 0.73 g |

Assuming that effective tumor formation by $10^7$ of ED-40515(−) in NOG mice was attributable to active neogenesis of tumoral vessels via CXCR4 of tumor cells, it has been expected that tumor formation would be inhibited as long as there was continuous administration of KRH-1636, a competitive agent of SDF-1 which was a ligand thereof in endothelial cells. However, in the case of ED-40515(−) and SLB-1 (histologically angiotropic) accompanied by bleeding, the mice formed tumors with sizes of 25×18×12 mm and 20×10×18 mm equivalent to those of non-treated group, even though KRH-1636 was intraperitoneally administered every day.

TABLE 11

Effect of CXDR4 antagonists on In Vivo Growth and Proliferation of HTLV-1 infected cell lines in NOG mice

| Cell line | group | No. of mice | Cells inoculated ($\times 10^7$) | Route of drug administration | Survival period (days) | Tumor size (mm) | Remarks |
|---|---|---|---|---|---|---|---|
| ED-40515(−) | Drug | 3 | 7.5 | intraperitoneally KRH-1636 0.14 mg/ | 15 | 25 × 18 × 12 | progressive large tumor |

TABLE 11-continued

Effect of CXDR4 antagonists on In Vivo Growth and Proliferation of HTLV-1 infected cell lines in NOG mice

| Cell line | group | No. of mice | Cells inoculated (×10[7]) | Route of drug administration | Survival period (days) | Tumor size (mm) | Remarks |
|---|---|---|---|---|---|---|---|
| | Control | 3 | 7.5 | mouse intraperitoneally medium 0.2 ml/mouse | 15 | 25 × 18 × 12 | progressive large tumor |
| SLB-1 | Drug | 3 | 7.5 | intraperitoneally KRH-1636 0.14 mg/mouse | 15 | 20 × 10 × 18 | progressive large tumor with hemorrhage |
| | Control | 3 | 7.5 | intraperitoneally medium 0.2 ml/mouse | 15 | 20 × 10 × 18 | progressive large tumor with hemorrhage |

Using Cytospin specimens of in vitro culture cells and frozen section specimens of in vivo tumor formative cells, both from ED-40515(−) and SLB-1, the immunostaining manners of CD4, CD8, CD3, CXCR4, CCR5 and SDF-1 were comparatively tested by enzyme antibody technique. All the cases of CD4, CD3, CXCR4 and SDF-1 were almost equally positive, and all the cases of CCR5 were negative. CD8 was negative in vitro, but positive in vivo. (Table 12)

TABLE 12

In vitro and in vivo examination of HTLV-1 infected cell line-transplanted NOG mice by FACS, WB, EMSA and immunohistochemistry Immunohistochemistry

| | CD4 | CD8 | CD3 | CXCR4 | CCR5 | SDF-1 |
|---|---|---|---|---|---|---|
| In-vitro | | | | | | |
| ED-40515(−) | ++ | − | + | + | − | ++ |
| SLB-1 | ++ | − | + | + | − | ++ |
| In-vivo | | | | | | |
| ED-40515(−) | +++ | + | + | + | − | +++ |
| SLB-1 | +++ | + | + | + | − | +++ |

+++ strongly positive
++ positive
+ weakly positive
− negative

Using in vitro culture cells and in vivo tumor formative cells of ED-40515(−), Table 13 Western blotting analyses on Tax, CXCR4, OX40 and OX40L were performed. All the cases of Tax were negative. However, all the cases of CXCR4, OX40 and OX40L were positive, and there was no significant difference in their strengths. (Table 13)

In vitro and in vivo examination of HTLV-1 infected cell line-transplanted NOG mice by FACS, WB, EMSA and immunohistochemistry Using in vitro culture cells and in vivo tumor formative cells of ED-40515(−), transcription factor activity of NFkB was examined by electrophoretic mobility shift assay (EMSA), though no difference therebetween was observed. (Table 14)

TABLE 14

In vitro and in vivo examination of HTLV-1 infected cell line-transplanted NOG mice by FACS, WB, EMSA and immunohistochemistry

| EMSA | In-vitro NFkB | In-vivo NFkB |
|---|---|---|
| ED-40515(−) | +++ | +++ |
| SLB-1 | +++ | |

The following points were recognized in the system wherein the transplant was conducted subcutaneously at posterior auricles of the NOG mice.

1) It was certainly confirmed that large tumors were formed in the NOG mice within very short periods, like 15 days after innoculation, which had not been expected. Conversely, NOD/Shi-scid mice (IL-2R γ chain[+/+]) did not form any tumors.

2) It was revealed that the NOG mice genetically delete NK cells, and therefore they did not require the pre-treatment against anti NK cells using monoclonal antibodies etc., which is essential in the case of C.B-17/Icr-scid or NOD/Shi-scid mice. (IL-2R γ chain[+/+])

3) The transplant was performed subcutaneously at a posterior auricle, that is, selecting a site which has a anatomically lower number of NK cells than an intraperitoneal site, and this allows a tumor to be easily formed. As a result, the size of the tumor was easily observed by appearance without need for incision.

4) Although Uchiyama et al. reported that MT-1, T-2 and TL-Oml did not form any tumors, in the present case relatively small tumors were formed in them. (Imada K, Takaori-Kondo A, Akagi T, Shimotohno K, Sugamura K, Hattori T, Yamabe H, Okuma M, Uchiyama T: Tumorigenicity of human T-cell leukemia virus type I-infected cell

| | In-vitro | | | | In-vivo | | | |
|---|---|---|---|---|---|---|---|---|
| WB | TAX | CXCR4 | OX40 | OX40L | TAX | CXCR4 | OX40 | OX40L |
| ED-40515(−) | − | ++ | + | + | − | + | + | + |
| SLB-1 | ++ | ++ | +++ | − | | | | | lines in severe combined immunodeficient mice and characterization of the cells proliferating in vivo. Blood 86:2350–7., 1995, Uchiyama,T: Human T cell leukemia virus type I (HTLV-I) and human diseases. Annu Rev Immunol 15:15–37, 1997)

Therefore, the system wherein the transplant is carried out subcutaneously at posterior auricles of the NOG mice, is an innovative tumor transplant system. Further, it was revealed that it could work in the same manner on B-cell tumors as well as on T-cell type tumors. Namely, these indicate also that this system is a valuable transplant system for the transplant of cancer cells or human normal lymphoid tissues.

In addition, when there is no laboratory animal model or it is difficult, even if there is, to put one into practical use, a human disease model can be established by transplanting human cells or tissues to this NOG mouse, thereby enabling disease researches, for which there has been no other choice but to be dependent on in vitro tests, with a test system which comes close to a limitless human in vivo test. Thus, this mouse is considered to make great contributions to the elucidation of mechanisms of disease onset, development of therapies etc. For example, irrespective of potent HAART therapy against HIV-1 infection, the rebound or mutant virus emergence of viremia is of primary importance. The reservoir of infectious viruses thereof is known to be FDC (follicular dendritic cells) of lymphatic follicle, and for researches on it, it is indispensable to establish a humanized model mouse to which lymphoid tissues including human lymphatic follicle are transplanted. For this, the present NOG mouse is useful.

Furthermore, with respect to a cause to make this system prone to form a tumor, examinations were made on what factor is increased or activated in transplanted cells, as compared with in vitro culture cells. All the cell lines used in the above examples were IL-2 independent, IL-2 producing, further Tax and CXCR4-SDF-1 system were revealed not to be directly associated therewith. However, within the search the present inventors have made, there was no factor except the above mentioned which the inventors recognized indicated a significant difference in comparison between in vitro culture cells and in vivo tumor-forming cells.

INDUSTRIAL APPLICABILITY

The present invention provides a method of producing NOG mice more suitable for engraftment of heterologous cells, particularly human cells, and a mouse produced by the method, as compared with an NOD/Shi-scid mouse and an NOD/LtSz-scid, $\beta$2m null mouse both conventionally known as an immunodeficient mouse. Transplanting human stem cells to the thus obtained mice enables a human stem cell assay system to be established. Further, transplanting human cells responsible for immunity enables human antibodies to be produced using the mouse of the present invention. Furthermore, a human tumor model mouse can be produced by transplanting and engrafting human tumors to the mouse, and the mouse can be used for therapies for tumors, screening of therapeutic agents and the like. Moreover, it is possible to produce an HIV or HTLV-1 infected model mouse to which an HIV or HTLV1 infected human lymphocyte is engrafted, and researches can be made on in vivo proliferation mechanism of HIV-1, HTLV-1 etc. Also, it is possible to conduct development of a therapy for virus infection, screening of a therapeutic agent for virus infection or the like.

All publications cited herein are incorporated herein with the whole contents thereof. Further, it is easily understood by those skilled in the art that various changes and modifications can be made in the invention without departing from the technical idea and scope described in the appended claims. It is intended that the present invention cover all such changes and modifications.

The invention claimed is:

1. A mouse produced by a method comprising backcrossing a mouse B with a mouse A, wherein said mouse A is a mouse obtained by backcrossing a C.B-17-scid mouse with an NOD/Shi mouse, and wherein said mouse B is an interleukin 2 receptor γ chain gene knockout mouse, wherein said mouse produced by the method does not express the interleukin 2 receptor γ chain, has an enhanced engraftment capacity of heterologous cells relative to a NOD/shi-scid mouse, has neither functional T-cells nor functional B-cells, exhibits reduced macrophage function relative to a NOD/shi-scid mouse, exhibits no NK cells or NK cell activity, and exhibits reduced dendritic function relative to a NOD/Shi-scid mouse.

2. The product mouse according to claim 1, wherein in said mouse transplanted human hematopoietic stem cells efficiently differentiate and proliferate without being eliminated.

3. A stem cell assay method comprising transplanting human hematopoietic stem cells to the product mouse according to claim 1 and analyzing cells that are differentiated and proliferated from the transplanted human hematopoietic stem cells.

4. The stem cell assay method according to claim 3, comprising analyzing the differentiation and proliferation of T-cells and B-cells from the transplanted human hematopoietic stem cells.

5. A method of proliferating human hematopoietic stem cells in the product mouse according to claim 1 comprising:
   transplanting and proliferating the human hematopoietic stem cells to and in said mouse;
   collecting human hematopoietic stem cells from bone marrow of the mouse; and
   repeatedly transplanting the collected human hematopoietic stem cells to the product mouse according to claim 4.

6. The method of proliferating human hematopoietic stem cells according to claim 5, wherein the frequency of repeating is at least three times.

7. The method according to claim 6, wherein the human hematopoietic stem cell has a foreign gene introduced thereinto.

8. The product mouse according to claim 1, wherein the mouse retains a human cell derived from HTLV-1 leukemia.

9. The mouse according to claim 8, wherein the mouse has the human tumor cell at an auricle thereof.

10. The product mouse according to claim 1 wherein the mouse retains a T-cell infected with HIV.

11. The product mouse according to claim 1, wherein the mouse retains a T-cell infected with HTLV-1.

12. The product mouse according to claim 1, wherein said mouse exhibits reduced dendritic function reduced to a NOD/Shi-scid mouse such that there is no detectable IFN-γ production in the mouse.

13. The mouse according to claim 12, wherein the production of IL-6 is reduced relative to a NOD/Shi-scid mouse.

14. A method of making a mouse according to claim 4 or claim 12, comprising backcrossing a mouse B with a mouse A, wherein said mouse A is a mouse obtained by backcrossing a C.B-17-scid mouse with an NOD/Shi mouse; and wherein said mouse B is an interleukin 2-receptor γ chain gene knockout mouse.

* * * * *

SEQUENCE LISTING

<160> NUMBER OF SEQ ID NOS: 3

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Primer PI.

<400> SEQUENCE: 1
ctgctcagaa tgatgcctcc aattcc                                    26

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Primer PII.

<400> SEQUENCE: 2
cctgcgtgca atccatcttg ttcaat                                    26

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Primer PIII.

```
<400> SEQUENCE: 3
gatccagatt gccaaggtga gtag                                          24
```